(12) United States Patent
Shulaker et al.

(10) Patent No.: US 12,422,399 B2
(45) Date of Patent: Sep. 23, 2025

(54) SYSTEMS, DEVICES, AND METHODS FOR GAS SENSING

(71) Applicant: Massachusetts Institute of Technology, Cambridge, MA (US)

(72) Inventors: Max Shulaker, Weston, MA (US); Mindy Deanna Bishop, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 18/662,578

(22) Filed: May 13, 2024

(65) Prior Publication Data
US 2024/0353369 A1    Oct. 24, 2024

Related U.S. Application Data

(62) Division of application No. 18/067,455, filed on Dec. 16, 2022, now Pat. No. 12,013,367, which is a division of application No. 16/973,249, filed as application No. PCT/US2019/036006 on Jun. 7, 2019, now Pat. No. 11,561,195.

(60) Provisional application No. 62/682,497, filed on Jun. 8, 2018.

(51) Int. Cl.
G01N 27/414    (2006.01)
G01N 33/497    (2006.01)

(52) U.S. Cl.
CPC ..... *G01N 27/4141* (2013.01); *G01N 27/4146* (2013.01); *G01N 33/497* (2013.01); *G01N 33/4977* (2024.05)

(58) Field of Classification Search
None
See application file for complete search history.

(56) References Cited

U.S. PATENT DOCUMENTS 6,191,724 B1    2/2001    McEwan
6,462,929 B2    10/2002   Compton et al.
7,598,544 B2    10/2009   Bertin et al.
(Continued)

FOREIGN PATENT DOCUMENTS

CN    101341488 A    1/2009
CN    102095769 A    6/2011
(Continued)

OTHER PUBLICATIONS

A formal semantics of the Risc-V ISA in Haskell. Github. Accessed at https://github.com/mit-plv/riscv-semantics on Feb. 13, 2020. 3 pages.
(Continued)

*Primary Examiner* — Erik Kielin
(74) *Attorney, Agent, or Firm* — Smith Baluch LLP

(57) ABSTRACT

A monolithic, three-dimensional (3D) integrated circuit (IC) device includes a sensing layer, a memory layer, and a processing layer. The sensing layer includes a plurality of carbon nanotube field-effect transistors (CNFETs) that are functionalized with at least 50 functional materials to generate data in response to exposure to a gas. The memory layer stores the data generated by the plurality of CNFETs, and the processing layer identifies one or more components of the gas based on the data generated by the plurality of CNFETs.

20 Claims, 14 Drawing Sheets
(13 of 14 Drawing Sheet(s) Filed in Color)

(56) References Cited

U.S. PATENT DOCUMENTS

| | | | |
|---|---|---|---|
| 7,859,385 | B2 | 12/2010 | Bertin et al. |
| 8,288,236 | B2 | 10/2012 | Chang et al. |
| 8,557,659 | B2 | 10/2013 | Teo et al. |
| 8,664,091 | B2 | 3/2014 | Zhu et al. |
| 8,685,815 | B2 | 4/2014 | Ahn et al. |
| 8,772,141 | B2 | 7/2014 | Afzali-Ardakani et al. |
| 8,785,911 | B2 | 7/2014 | Chen et al. |
| 8,946,007 | B2 | 2/2015 | Doris et al. |
| 9,209,288 | B2 | 12/2015 | Avci et al. |
| 9,613,879 | B2 | 4/2017 | Hersam et al. |
| 10,256,320 | B1 | 4/2019 | Liu et al. |
| 11,062,067 | B2 | 7/2021 | Hills et al. |
| 11,271,160 | B2 | 3/2022 | Lau et al. |
| 11,561,195 | B2 | 1/2023 | Shulaker et al. |
| 2004/0006257 | A1* | 1/2004 | Burch ............ A61B 5/00 600/300 |
| 2004/0099438 | A1 | 5/2004 | Arthur et al. |
| 2005/0181587 | A1 | 8/2005 | Duan et al. |
| 2005/0245836 | A1 | 11/2005 | Star et al. |
| 2006/0115640 | A1 | 6/2006 | Yodh et al. |
| 2006/0183278 | A1 | 8/2006 | Bertin et al. |
| 2006/0204427 | A1 | 9/2006 | Ghenciu et al. |
| 2007/0281409 | A1 | 12/2007 | Zhang et al. |
| 2008/0099842 | A1 | 5/2008 | Gyoujin et al. |
| 2008/0210987 | A1 | 9/2008 | Bondavalli et al. |
| 2009/0184346 | A1 | 7/2009 | Jain |
| 2009/0230300 | A1* | 9/2009 | Trevejo ............ C12Q 1/04 73/23.3 |
| 2010/0111813 | A1 | 5/2010 | Fan |
| 2010/0207208 | A1 | 8/2010 | Bedell et al. |
| 2011/0045660 | A1 | 2/2011 | Romano et al. |
| 2011/0147715 | A1 | 6/2011 | Rogers et al. |
| 2011/0201956 | A1 | 8/2011 | Alferness et al. |
| 2012/0089041 | A1 | 4/2012 | Schlager |
| 2012/0129273 | A1 | 5/2012 | Johnson, Jr. et al. |
| 2012/0129301 | A1 | 5/2012 | Or-Bach et al. |
| 2012/0326126 | A1 | 12/2012 | Chen et al. |
| 2013/0122690 | A1 | 5/2013 | Zhu et al. |
| 2013/0134394 | A1 | 5/2013 | Zhou et al. |
| 2014/0008606 | A1 | 1/2014 | Hussain et al. |
| 2014/0017886 | A1 | 1/2014 | Teo et al. |
| 2014/0175376 | A1 | 6/2014 | Avci et al. |
| 2014/0336080 | A1* | 11/2014 | Ruether ............ C12Q 1/14 435/36 |
| 2015/0227669 | A1 | 8/2015 | Joshi et al. |
| 2015/0318504 | A1 | 11/2015 | Xiao |
| 2015/0370948 | A1 | 12/2015 | Kawa et al. |
| 2016/0077047 | A1 | 3/2016 | Khamis et al. |
| 2016/0123919 | A1 | 5/2016 | Johnson et al. |
| 2016/0133843 | A1 | 5/2016 | Rogers et al. |
| 2016/0147934 | A1 | 5/2016 | Keller et al. |
| 2016/0148074 | A1 | 5/2016 | Jean et al. |
| 2016/0190492 | A1 | 6/2016 | Li et al. |
| 2017/0005140 | A1 | 1/2017 | Bertin |
| 2017/0059514 | A1 | 3/2017 | Hoffman |
| 2017/0162710 | A1 | 6/2017 | Shih et al. |
| 2017/0179283 | A1 | 6/2017 | Pourghaderi et al. |
| 2017/0294583 | A1 | 10/2017 | Liang et al. |
| 2018/0089531 | A1 | 3/2018 | Geva et al. |
| 2019/0167152 | A1 | 6/2019 | Weda et al. |
| 2019/0189775 | A1 | 6/2019 | Liu et al. |
| 2019/0271685 | A1* | 9/2019 | Haick ............ A61B 5/08 |
| 2019/0341450 | A1 | 11/2019 | Lee et al. |
| 2019/0378998 | A1 | 12/2019 | Sakii et al. |
| 2020/0082032 | A1 | 3/2020 | Hills et al. |
| 2021/0050417 | A1 | 2/2021 | Shulaker et al. |
| 2021/0247356 | A1 | 8/2021 | Shulaker et al. |
| 2021/0282678 | A1* | 9/2021 | Haick ............ G01N 33/4975 |
| 2021/0294959 | A1 | 9/2021 | Hills et al. |
| 2021/0313530 | A1 | 10/2021 | Lau et al. |
| 2021/0351354 | A1 | 11/2021 | Lau et al. |
| 2022/0284077 | A1 | 9/2022 | Dahl et al. |

FOREIGN PATENT DOCUMENTS

| | | |
|---|---|---|
| CN | 104778324 A | 7/2015 |
| CN | 106233464 A | 12/2016 |
| CN | 106462549 A | 2/2017 |
| EP | 0190070 B1 | 8/1992 |
| WO | 2014113722 A1 | 7/2014 |
| WO | 2017001406 A3 | 4/2017 |

OTHER PUBLICATIONS

Aly et al., "Energy-efficient abundant-data computing: The N3XT 1,000 x." Computer 48.12 (2015): 24-33.

Aly et al., "The N3XT approach to energy-efficient abundant-data computing." Proceedings of the IEEE 107.1 (2018): 19-48.

Appenzeller, Carbon Nanotubes for High-Performance Electronics—Progress and Prospect. Proc. IEEE 2008, 96, 201-211.

Aria et al., Parameter Space of Atomic Layer Deposition of Ultrathin Oxides on Graphene. ACS Appl. Mater. Interfaces 2016, 8, 30564-30575.

Asanovic et al., The berkeley out-of-order machine (boom): An industry-competitive, synthesizable, parameterized risc-v processor. No. UCB-EECS-2015-167. University of California at Berkeley Berkeley United States, 2015. 5 pages.

Bardon et al., "Extreme scaling enabled by 5 tracks cells: Holistic design-device co-optimization for FinFETs and lateral nanowires." Electron Devices Meeting (IEDM), 2016 IEEE International. IEEE, 2016, 4 pages.

Batude et al., "Advances, challenges and opportunities in 3D CMOS sequential integration." 2011 International Electron Devices Meeting. IEEE, 2011. 4 pages.

Boots et al., "Identification of microorganisms based on headspace analysis of volatile organic compounds by gas chromatography-mass spectrometry." Journal of breath research 8.2 (2014): 027106. 13 pages.

Bos et al., "The volatile metabolic fingerprint of ventilator-associated pneumonia." Intensive care medicine 40.5 (2014): 761-762.

Bos et al., "Volatile metabolites of pathogens: a systematic review." PLoS pathog 9.5 (2013): e1003311. 8 pages.

Brady et al., "Polyfluorene-sorted, carbon nanotube array field-effect transistors with increased current density and high on/off ratio." ACS nano 8.11 (2014): 11614-11621.

Brady et al., "Quasi-ballistic carbon nanotube array transistors with current density exceeding Si and GaAs." Science advances 2.9 (2016): e1601240. 10 pages.

Cao et al., "Arrays of single-walled carbon nanotubes with full surface coverage for high-performance electronics." Nature nanotechnology 8.3 (2013): 180. 7 pages.

Cao et al., "End-bonded contacts for carbon nanotube transistors with low, size-independent resistance." Science350.6256 (2015): 68-72.

Cao et al., "Medium-scale carbon nanotube thin-film integrated circuits on flexible plastic substrates." Nature 454.7203 (2008): 495-500.

Cao et al., Carbon Nanotube Transistors Scaled to a 40-Nanometer Footprint. Science 2017, 356, 1369-1372.

Chen et al., "Externally assembled gate-all-around carbon nanotube field-effect transistor." IEEE electron device letters 29.2 (2008): 183-185.

Chen et al., The Role of Metal-Nanotube Contact in the Performance of Carbon Nanotube Field-Effect Transistors. Nano Lett. 2005, 5, 1497-1502.

Chen, A Breath Sensor Based on Carbon Nanotubes and System Design, Journal of Zhengzhou University (Natural Science Edition) Year 2010, Issue 3, pp. 80-83.

Chinese Notification of Allowance and Search Report with English Translation in Chinese Application No. 201980058941.1 dated Jun. 1, 2022, 6 pages.

Clark et al., "ASAP7: A 7-nm finFET predictive process design kit." Microelectronics Journal 53 (2016): 105-115.

Cook, "Ventilator associated pneumonia: perspectives on the burden of illness." Intensive care medicine 26.1 (2000): S031-S037.

(56) References Cited

OTHER PUBLICATIONS

Deng et al., "Carbon nanotube transistor circuits: Circuit-level performance benchmarking and design options for living with imperfections." Solid-State Circuits Conference, 2007. ISSCC 2007. Digest of Technical Papers. IEEE International. IEEE, 2007. 3 pages.
Desai et al., "MoS2 transistors with 1-nanometer gate lengths." Science 354.6308 (2016): 99-102.
Design Compiler Graphical. Synopsys, Inc. Accessed at https://www.synopsys.com/implementation-and-signoff/rtl-synthesis-test/design-compiler-graphical.html on Mar. 2, 2021. 6 pages.
Ding et al., "CMOS-based carbon nanotube pass-transistor logic integrated circuits." Nature communications 3.1 (2012): 1-7.
Ding et al., "Y-contacted high-performance n-type single-walled carbon nanotube field-effect transistors: scaling and comparison with Sc-contacted devices." Nano letters 9.12 (2009): 4209-4214.
Ebrahimi et al. "Monolithic 3D integration advances and challenges: From technology to system levels." 2014 SOI-3D-Subthreshold Microelectronics Technology Unified Conference (S3S). IEEE, 2014, 2pages.
Examiner Report in European app. No. 19814933.8 dated Nov. 9, 2023, 5 pages.
Extended European Search Report in European Patent Application No. 19814933.8 dated Dec. 23, 2021, 8 pages.
Farmer et al., "Atomic layer deposition on suspended single-walled carbon nanotubes via gas-phase noncovalent functionalization." Nano letters 6.4 (2006): 699-703.
Filipiak et al., "Molecular analysis of volatile metabolites released specifically by *Staphylococcus aureus* and Pseudomonas aeruginosa." BMC microbiology 12.1 (2012): 1-16.
Fowler et al., "Critical care capacity in Canada: results of a national cross-sectional study." Critical care 19.1 (2015): 1-8.
Fowler et al., "Surveillance for lower airway pathogens in mechanically ventilated patients by metabolomic analysis of exhaled breath: a case-control study." Thorax 70.4 (2015): 320-325.
Franklin et al., "Carbon nanotube complementary wrap-gate transistors." Nano letters 13.6 (2013): 2490-2495.
Franklin et al., "Scalable and fully self-aligned n-type carbon nanotube transistors with gate-all-around." Electron Devices Meeting (IEDM), 2012 IEEE International. IEEE, 2012. 4 pages.
Franklin et al., "Sub-10 nm carbon nanotube transistor." Nano letters 12.2 (2012): 758-762.
Geier et al., "Controlled n-type doping of carbon nanotube transistors by an organorhodium dimer." Nano letters 16.7 (2016): 4329-4334.
Geier et al., "Solution-processed carbon nanotube thin-film complementary static random access memory." Nature nanotechnology 10.11 (2015): 944. 6 pages.
Geier et al., Subnanowatt Carbon Nanotube Complementary Logic Enabled by Threshold Voltage Control. Nano Lett. 2013, 13, 4810-4814.
Gouma et al., "Novel isoprene sensor for a flu virus breath monitor." Sensors 17.1 (2017): 199. 7 pages.
Ha et al., Highly Uniform and Stable N-Type Carbon Nanotube Transistors by Using Positively Charged Silicon Nitride Thin Films. Nano Lett. 2015, 15, 392-397.
Hahn et al., "A scaled replacement metal gate InGaAs-on-Insulator n-FinFET on Si with record performance." Electron Devices Meeting (IEDM), 2017 IEEE International. IEEE, 2017. 4 pages.
Han et al., "High-speed logic integrated circuits with solution-processed self-assembled carbon nanotubes." Nature nanotechnology 12.9 (2017): 861. 7 pages.
Heinze et al., Carbon Nanotubes as Schottky Barrier Transistors. Phys. Rev. Lett. 2002, 89, 106801. 4 pages.
High Purity, Electronically Separated Nanomaterials. NanoIntegris. Accessed at http://nanointegris.com/ on Feb. 13, 2020. 8 pages.
Hills et al., "Rapid Co-Optimization of Processing and Circuit Design to Overcome Carbon Nanotube Variations." IEEE Trans. on CAD of Integrated Circuits and Systems 34.7 (2015): 1082-1095.

Hills et al., "TRIG: hardware accelerator for inference-based applications and experimental demonstration using carbon nanotube FETs." Proceedings of the 55th Annual Design Automation Conference. 2018. 10 pages.
Hills et al., "Understanding energy efficiency benefits of carbon nanotube field-effect transistors for digital VLSI." IEEE Transactions on Nanotechnology 17.6 (2018): 1259-1269.
Xu et al., "Efficient and reversible electron doping of semiconductor-enriched single-walled carbon nanotubes by using decamethylcobaltocene." Scientific reports 7.1 (2017): 1-10.
Yakimets et al., "Power aware FinFET and lateral nanosheet FET targeting for 3nm CMOS technology." Electron Devices Meeting (IEDM), 2017 IEEE International. IEEE, 2017. 4 pages.
Yang et al., "High-performance complementary transistors and medium-scale integrated circuits based on carbon nanotube thin films." ACS nano 11.4 (2017): 4124-4132.
Yoshida et al., "Highly conductive metal gate fill integration solution for extremely scaled RMG stack for 5 nm & beyond." Electron Devices Meeting (IEDM), 2017 IEEE International. IEEE, 2017. 4 pages.
Zhang et al. "Carbon nanotube correlation: Promising opportunity for CNFET circuit yield enhancement." Proceedings of the 47th Design Automation Conference (DAC) 2010, p. 889-892.
Zhang et al., "Doping-free fabrication of carbon nanotube based ballistic CMOS devices and circuits." Nano Letters 7.12 (2007): 3603-3607.
Zhang et al., "High-performance carbon nanotube complementary electronics and integrated sensor systems on ultrathin plastic foil." ACS nano 12.3 (2018): 2773-2779.
Zhang et al., "Selective etching of metallic carbon nanotubes by gas-phase reaction." Science 314.5801 (2006): 974-977.
Zhang et al., Air-Stable Conversion of Separated Carbon Nanotube Thin-Film Transistors from p-Type to n-Type Using Atomic Layer Deposition of High-? Oxide and Its Application in CMOS Logic Circuits. ACS Nano 2011, 5, 3284-3292.
Zhao et al., "Sub-10 nm diameter InGaAs vertical nanowire MOSFETs." Electron Devices Meeting (IEDM), 2017 IEEE International. IEEE, 2017. 4 pages.
Zhong et al., "Solution-processed carbon nanotubes based transistors with current density of 1.7 mA/µm and peak transconductance of 0.8 mS/µm." 2017 IEEE International Electron Devices Meeting (IEDM). IEEE, 2017. 5 pages.
Rai et al., Air Stable Doping and Intrinsic Mobility Enhancement in Monolayer Molybdenum Disulfide by Amorphous Titanium Suboxide Encapsulation. Nano Lett. 2015, 15, 4329-4336.
Rai et al., Interfacial-Oxygen-Vacancy Mediated Doping of MoS2 by high-k dielectrics. In 2015 73rd Annual Device Research Conference (DRC); IEEE, 2015; 189-190.
Rana et al., "A review on recent advances of CNTs as gas sensors." Sensor Review (2017). 12 pages.
Sabry et al., Energy-Efficient Abundant-Data Computing: The N3XT 1,000x. Computer (Long. Beach. Calif). 2015, 48, 24-33.
Safdar et al., "The pathogenesis of ventilator-associated pneumonia: its relevance to developing effective strategies for prevention." Respiratory care 50.6 (2005): 725-741.
Schnabel et al. "Analysis of volatile organic compounds in exhaled breath to diagnose ventilator-associated pneumonia." Scientific Reports 5.1 (2015): 1-10.
Schnabel et al., "Electronic nose analysis of exhaled breath to diagnose ventilator-associated pneumonia." Respiratory medicine 109.11 (2015): 1454-1459.
Second Office Action (with translation) in Chinese App. 201980050247.5 dated Jun. 21, 2023, 15 pages.
Semiconductor Industry Association. "International Technology Roadmap for Semiconductors (2013)." Downloaded from http://www.itrs2.net/itrs-reports.html on Feb. 24, 2020. 237 pages.
Sentaurus Device. Synopsys, Inc.. Accessed at https://www.synopsys.com/silicon/tcad/device-simulation/sentaurus- device.html on Mar. 2, 2021. 3 pages.
Seo et al., "A 10nm platform technology for low power and high performance application featuring FINFET devices with multi workfunc-

(56) References Cited

OTHER PUBLICATIONS tion gate stack on bulk and SOI." VLSI Technology (VLSI-Technology): Digest of Technical Papers, 2014 Symposium on. IEEE, 2014. 2 pages.
Shahrjerdi et al., "High-performance air-stable n-type carbon nanotube transistors with erbium contacts." ACS nano 7.9 (2013): 8303-8308.
Sherazi et al. "Track height reduction for standard-cell in below 5nm node: how low can you go?. " Design-Process- Technology Co-optimization for Manufacturability XII. vol. 10588. SPIE, 2018, 14 pages.
Shulaker et al., "Carbon nanotube circuit integration up to sub-20 nm channel lengths." ACS nano 8.4 (2014): 3434-3443.
Shulaker et al., "Efficient metallic carbon nanotube removal for highly-scaled technologies." 2015 IEEE International Electron Devices Meeting (IEDM). IEEE, 2015. 4 pages.
Shulaker et al., "Monolithic 3D integration of logic and memory: Carbon nanotube FETs, resistive RAM, and silicon FETs." 2014 IEEE International Electron Devices Meeting. IEEE, 2014. 4 pages.
Shulaker et al., "Monolithic three-dimensional integration of carbon nanotube FETs with silicon CMOS." 2014 Symposium on VLSI Technology (VLSI-Technology): Digest of Technical Papers. IEEE, 2014. 2 pages.
Shulaker et al., "Sensor-to-digital interface built entirely with carbon nanotube FETs." IEEE Journal of Solid-State Circuits 49.1 (2013): 190-201.
Shulaker et al., "Three-dimensional integration of nanotechnologies for computing and data storage on a single chip." Nature 547.7661 (2017), 19 pages.
Shulaker et al., Carbon Nanotube Computer. Nature 2013, 501, 526-530.
Shulaker et al., Experimental Demonstration of a Fully Digital Capacitive Sensor Interface Built Entirely Using Carbon-Nanotube FETs. In 2013 IEEE International Solid-State Circuits Conference Digest of Technical Papers; IEEE, 2013; 112-113.
Shulaker et al., High-Performance Carbon Nanotube Field-Effect Transistors. In 2014 IEEE International Electron Devices Meeting; IEEE, 2014; 33.6.1-33.6.4.
Shulaker et al., Linear Increases in Carbon Nanotube Density Through Multiple Transfer Technique. Nano Lett. 2011, 11, 1881-1886.
Si et al., "Scalable preparation of high-density semiconducting carbon nanotube arrays for high-performance field-effect transistors." ACS nano 12.1 (2018): 627-634.
Smolinska, et al. "Current breathomics—a review on data pre-processing techniques and machine learning in metabolomics breath analysis." Journal of breath research 8.2 (2014): 027105, 21 pages.
Spectre Simulation Platform. Cadence Design Systems, Inc. Accessed at https://www.cadence.com/en_US/home/tools/custom-ic-analog-rf-design/circuit-simulation/spectre-simulation-platform.html on Mar. 2, 2021. 3 pages.
Spike, a RISC-V ISA Simulator. Github. Accessed at https://github.com/riscv/riscv-isa-sim on Feb. 13, 2020. 6 pages.
Suriyasena Liyanage et al., VLSI-Compatible Carbon Nanotube Doping Technique with Low Work-Function Metal Oxides. Nano Lett. 2014, 14, 1884-1890.
Tang et al., Flexible CMOS Integrated Circuits Based on Carbon Nanotubes with Sub-10 ns Stage Delays. Nat. Electron. 2018, 1, 191-196.
Tans et al., "Room-temperature transistor based on a single carbon nanotube." Nature 393.6680 (1998): 49-52.
TCAD—Raphael. Synopsys, Inc. Accessed at https://www.synopsys.com/silicon/tcad/interconnect-simulation/raphael.html on Mar. 2, 2021. 4 pages.
Tracer—Electron scattering and process effects quantified. GenISys GmbH 2017. Accessed at https://www.genisys-gmbh.com/tracer.html on Mar. 2, 2021. 6 pages.
TruNarc. HazmatLINK. Accessed at http://www.hazmatlink.com/trunarc.html on Mar. 2, 2021. 2 pages.
Tulevski et al., "High purity isolation and quantification of semiconducting carbon nanotubes via column chromatography." ACS nano 7.4 (2013): 2971-2976.
Tulevski et al., "Toward high-performance digital logic technology with carbon nanotubes." ACS nano 8.9 (2014): 8730-8745.
Understand, Predict, and Optimize Physics-Based Designs and Processes with COMSOL Multiphysics®. Comsol Multiphysics®. Accessed at https://www.comsol.com/comsol-multiphysics on Mar. 2, 2021. 16 pages.
Valsaraj et al., Theoretical and Experimental Investigation of Vacancy-Based Doping of Monolayer MoS 2 on Oxide. 2D Mater. 2015, 2, 045009. 12 pages.
Venkatachalam et al., "The diagnostic dilemma of ventilator-associated pneumonia in critically ill children." Pediatric Critical Care Medicine 12.3 (2011): 286-296.
Vinet et al., "3D monolithic integration: Technological challenges and electrical results." Microelectronic Engineering88.4 (2011): 331-335.
Wang et al., "Growing highly pure semiconducting carbon nanotubes by electrotwisting the helicity." Nature Catalysis 1.5 (2018): 326-331.
Wang et al., "National trends in patient safety for four common conditions, 2005-2011." N Engl J Med 370 (2014): 341-351.
Wei et al. "A non-iterative compact model for carbon nanotube FETs incorporating source exhaustion effects." 2009 IEEE International Electron Devices Meeting (IEDM). IEEE, 2009. 4 pages.
Wei et al. Carbon nanotube circuits: Opportunities and challenges. EDAA (2013)IEEE, 2013. 6 pages.
Western Digital to Accelerate the Future of Next-Generation Computing Architectures for Big Data and Fast Data Environments. Western Digital Nov. 28, 2017. Accessed at https://www.westerndigital.com/company/newsroom/press-releases/2017/2017-11-28-western-digital-to-accelerate-the-future-of-next-generation-computing-architectures-for-big-data-and-fast-data-environments. 7 pages.
Wolf, RISC-V Formal Verification Framework. Github. Accessed at https://github.com/cliffordwolf/riscv-formal. 2 pages.
Wolf, SymbiYosys (sby)—Front-end for Yosys-based formal verification flows. Github. Accessed at https://github.com/YosysHQ/SymbiYosys on Feb. 13, 2020. 1 pages.
Won et al., "Zipping, entanglement, and the elastic modulus of aligned single-walled carbon nanotube films." Proceedings of the National Academy of Sciences 110.51 (2013): 20426-20430.
Wong et al., "Memory leads the way to better computing." Nature nanotechnology 10.3 (2015): 191-194.
Wu et al., "Brain-inspired computing exploiting carbon nanotube FETs and resistive RAM: Hyperdimensional computing case study." 2018 IEEE International Solid-State Circuits Conference-(ISSCC). IEEE, 2018, pp. 492-494.
Wu et al., "Hyperdimensional computing exploiting carbon nanotube FETs, resistive RAM, and their monolithic 3D integration." IEEE Journal of Solid-State Circuits 53.11 (2018): 3183-3196.
Hills et al., Modern microprocessor built from complementary carbon nanotube transistors. Nature 572.7771 (2019): 595-602.
Humphreys et al., "Electronic nose analysis of bronchoalveolar lavage fluid." European journal of clinical investigation 41.1 (2011): 52-58.
IC Compiler II. Synopsys, Inc. Accessed at https://www.synopsys.com/implementation-and-signoff/physical-implementation/ic-compiler.html on Mar. 2, 2021. 6 pages.
International Search Report and Written Opinion in International Application No. PCT/US2019/050286 mailed May 19, 2020, 16 pages.
International Search Report and Written Opinion in International Patent Application No. PCT/US19/15595 mailed Apr. 19, 2019, 14 pages.
International Search Report and Written Opinion in International Patent Application No. PCT/US2019/036006 mailed Oct. 16, 2019, 13 pages.
International Search Report and Written Opinion in International Patent Application No. PCT/US2019/052675 mailed Jan. 14, 2020, 16 pages.

(56) References Cited

OTHER PUBLICATIONS

International Search Report and Written Opinion in International Patent Application No. PCT/US2019/063932 mailed Feb. 19, 2020, 14 pages.
Javey et al., "Ballistic carbon nanotube field-effect transistors." nature 424.6949 (2003): 654-657.
Joo et al., Dose-Controlled, Floating Evaporative Self-Assembly and Alignment of Semiconducting Carbon Nanotubes from Organic Solvents. Langmuir 2014, 30, 3460-3466.
Kalil et al., "Executive summary: management of adults with hospital-acquired and ventilator-associated pneumonia: 2016 clinical practice guidelines by the Infectious Diseases Society of America and the American Thoracic Society." Clinical Infectious Diseases 63.5 (2016): 575-582.
Kalil et al., "Management of adults with hospital-acquired and ventilator-associated pneumonia: 2016 clinical practice guidelines by the Infectious Diseases Society of America and the American Thoracic Society." Clinical Infectious Diseases 63.5 (2016): e61-e111, 51 pages.
Kang et al., CMOS digital integrated circuits. Tata McGraw-Hill Education, 2003. 83 pages.
Khan et al., "Science and research policy at the end of Moore's law." Nature Electronics 1.1 (2018): 14-21.
Kim et al., "Atomic layer deposited Al 2 O 3 for gate dielectric and passivation layer of single-walled carbon nanotube transistors." Applied physics letters 90.16 (2007): 163108. 4 pages.
Koenig et al., "Ventilator-associated pneumonia: diagnosis, treatment, and prevention." Clinical microbiology reviews 19.4 (2006): 637-657.
Kollef et al., "Economic impact of ventilator-associated pneumonia in a large matched cohort." (2012). 9 pages.
Kuhn et al., The Ultimate CMOS Device and Beyond. In IEEE Int. Electron Devices Meet.; 2012; vol. 8.1.1?8.1. 4 pages.
Kuhn,. "Considerations for ultimate CMOS scaling." IEEE transactions on Electron Devices 59.7 (2012): 1813-1828.
Kuti et al., "Impact of inappropriate antibiotic therapy on mortality in patients with ventilator-associated pneumonia and blood stream infection: a meta-analysis." Journal of critical care 23.1 (2008): 91-100.
La Tulipe et al., "Upside-down FETS." SOI Conference, 2008. SOI. IEEE International. IEEE, 2008. 2 pages.
Lau et al., "Tunable n-type doping of carbon nanotubes through engineered atomic layer deposition HfOX films." ACS nano 12.11 (2018): 10924-10931.
Lee et al., "A compact virtual-source model for carbon nanotube FETs in the sub-10-nm regime—Part I: Intrinsic elements." IEEE transactions on electron devices 62.9 (2015): 3061-3069.
Li et al., "Facile method for enhancing conductivity of printed carbon nanotubes electrode via simple rinsing process." Organic Electronics 47 (2017): 174-180.
Library Design. Silvaco, Inc. Accessed at https://silvaco.com/services/library-design/ on Mar. 2, 2021. 4 pages. .
Liebmann et al., "Overcoming scaling barriers through design technology cooptimization." VLSI Technology, 2016 IEEE Symposium on. IEEE, 2016. 2 pages.
Lin et al., "ACCNT—A metallic-CNT-tolerant design methodology for carbon-nanotube VLSI: Concepts and experimental demonstration." IEEE Transactions on Electron Devices 56.12 (2009): 2969-2978.
Liu et al., Carbon Nanotube-Based Three-Dimensional Monolithic Optoelectronic Integrated System. Nat. Commun. 2017, 8, 15649. 8 pages.
Machado et al., "Cost-effectiveness of linezolid versus vancomycin in mechanical ventilation-associated nosocomial pneumonia caused by methicillin-resistant *Staphylococcus aureus*." Brazilian Journal of Infectious Diseases 9.3 (2005): 191-200.
Markov et al., "Progress and challenges in VLSI placement research." Proceedings of the IEEE 103.11 (2015): 1985-2003.
McClellan et al., Effective N-Type Doping of Monolayer MoS2 by AlOx. In 2017 75th Annual Device Research Conference (DRC); IEEE, 2017; 1-2.
Melsen et al., "Attributable mortality of ventilator-associated pneumonia: a meta-analysis of individual patient data from randomised prevention studies." The Lancet infectious diseases 13.8 (2013): 665-671.
Mistry, 10 nm Technology Leadership. Leading at the edge technology and manufacturing day 2017. Intel. Accessed at https://newsroom.intel.com/newsroom/wp-content/uploads/sites/11/2017/03/Kaizad-Mistry-2017-Manufacturing.pdf. 37 pages.
Muscedere et al., "Mortality, attributable mortality, and clinical events as end points for clinical trials of ventilator- associated pneumonia and hospital-acquired pneumonia." Clinical infectious diseases 51.Supplement_1 (2010): S120-S125.
Nakhleh et al., "Diagnosis and classification of 17 diseases from 1404 subjects via pattern analysis of exhaled molecules." ACS nano 11.1 (2017): 112-125.
Narasimha et al., "A 7nm CMOS technology platform for mobile and high performance compute application." Electron Devices Meeting (IEDM), 2017 IEEE International. IEEE, 2017. 4 pages.
Niemetz, et al., Boolector 2.0. Journal on Satisfiability, Boolean Modeling and Computation 9 (2015) 53-58.
Nourbakhsh et al., "MoS2 field-effect transistor with sub-10 nm channel length." Nano letters 16.12 (2016): 7798-7806.
NVIDIA RISC-V Story. NVIDIA 4th RISC-V Workshop Jul. 2016. Accessed at https://riscv.org/wp-content/uploads/2016/07/Tue1100_Nvidia_RISCV_Story_V2.pdf. 15 pages.
Office Action (Rejection) and Search Report (with translation) in Chinese App. 201980050247.5 dated Mar. 8, 2024, 25 pages.
Office Action and Search Report (with translation) in Chinese App. 201980050247.5 dated Dec. 5, 2022, 21 pages.
Open Source RISC-V Cores and Tools. Bluespec. Accessed at https://bluespec.com/ on Feb. 13, 2020. 5 pages.
OpenSPARC Overview. Oracle Accessed at http://www.opensparc.net/opensparc-t2 on Feb. 13, 2020. 1 pages.
Patil et al., "VMR: VLSI-compatible metallic carbon nanotube removal for imperfection-immune cascaded multi-stage digital logic circuits using carbon nanotube FETs." 2009 IEEE International Electron Devices Meeting (IEDM). IEEE, 2009. 4 pages.
Patil et al., "Wafer-scale growth and transfer of aligned single-walled carbon nanotubes." IEEE Transactions on Nanotechnology 8.4 (2009): 498-504.
Patterson, "50 Years of computer architecture: From the mainframe CPU to the domain-specific tpu and the open RISC-V instruction set." 2018 IEEE International Solid-State Circuits Conference-(ISSCC). IEEE, 2018. 5 pages.
Phillips et al., "Variation in volatile organic compounds in the breath of normal humans." Journal of Chromatography B: Biomedical Sciences and Applications 729.1-2 (1999): 75-88.
Prakash et al., Understanding Contact Gating in Schottky Barrier Transistors from 2D Channels. Sci. Rep. 2017, 7, 12596. 9 pages.
PrimeTime Static Timing Analysis. Synopsys, Inc. Accessed at https://www.synopsys.com/implementation-and-signoff/signoff/primetime.html on Mar. 2, 2021. 7 pages.
Qiu et al., "Scaling carbon nanotube complementary transistors to 5-nm gate lengths." Science355.6322 (2017): 271-276.

* cited by examiner

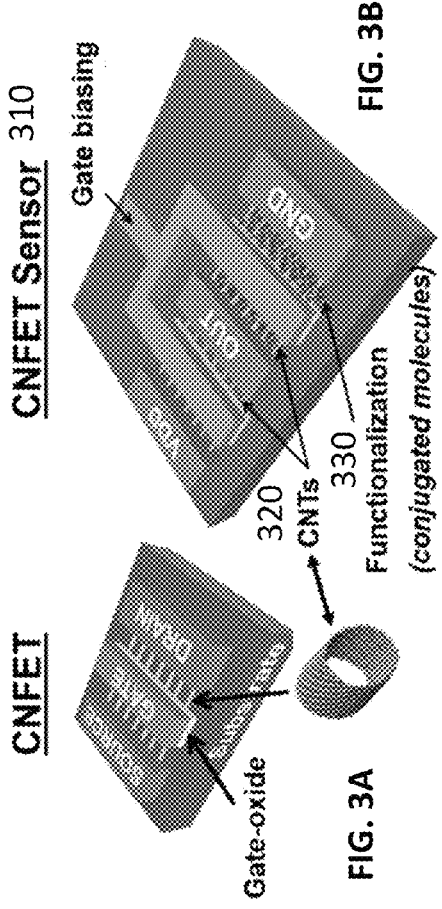
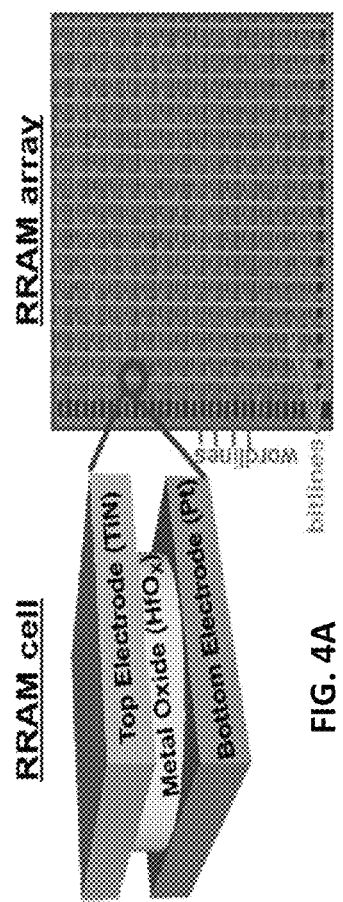

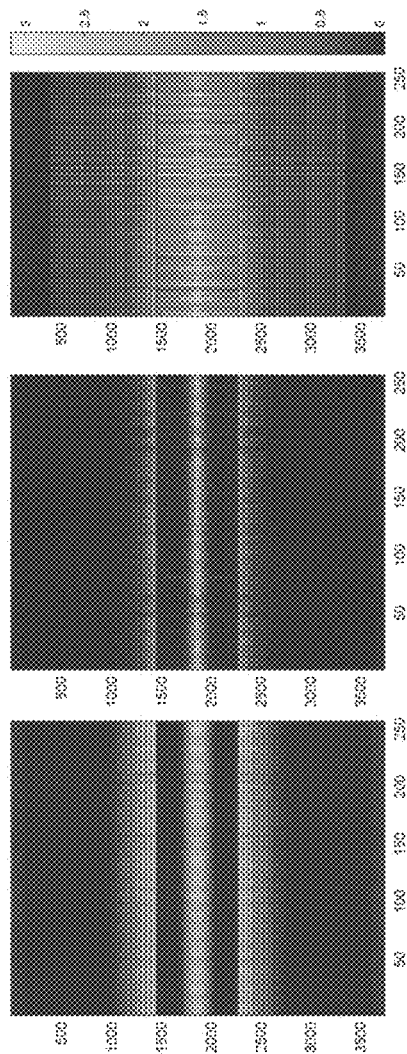
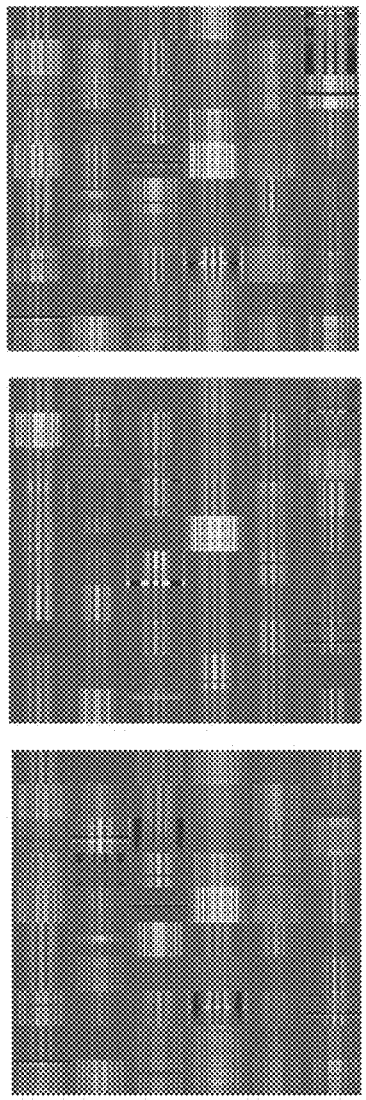
FIG. 13C
FIG. 13B
FIG. 13A
FIG. 13F
FIG. 13E
FIG. 13D

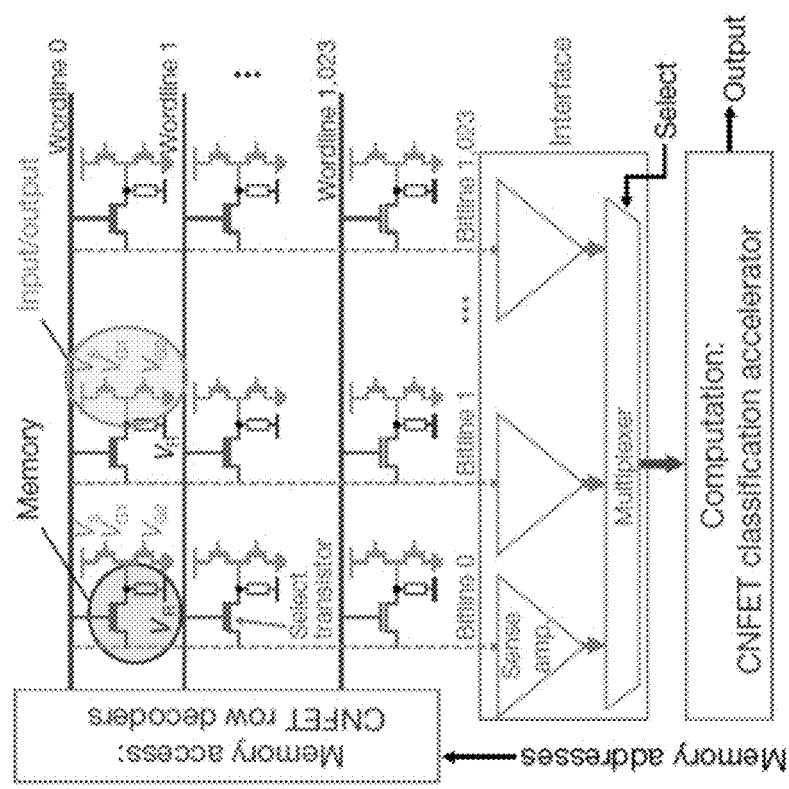
FIG. 15B
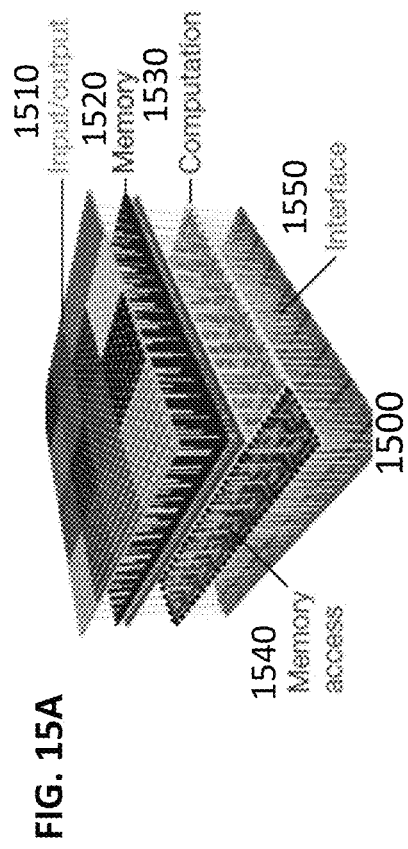
FIG. 15A
FIG. 15C

SYSTEMS, DEVICES, AND METHODS FOR GAS SENSING

CROSS-REFERENCE TO RELATED APPLICATIONS

This application is a divisional of U.S. application Ser. No. 18/067,455, filed Dec. 16, 2022, which is a divisional of U.S. application Ser. No. 16/973,249, filed on Dec. 8, 2020, which is a U.S. National Stage Application under 35 USC 371 of International Application No. PCT/US2019/036006, filed on Jun. 7, 2019, which claims the priority benefit, under 35 U.S.C. § 119(e), of U.S. Application No. 62/682,497, which was filed on Jun. 8, 2018, with each application being incorporated herein by reference in its entirety.

BACKGROUND

Gas detection is critical for a wide range of impactful applications ranging from healthcare (e.g., point-of-care diagnostics based on breath analysis), to threat detection (e.g., discovering hidden explosives or chemical weapons), to toxin detection (e.g., detecting fentanyl, an extremely potent and dangerous synthetic opioid). However, these applications present major challenges for conventional sensing systems today. State-of-the-art gas chromatography and mass spectrometry systems are large, high power (i.e., not wearable or handheld), and expensive.

Alternatively, developing highly-specific portable gas sensors that are engineered to react with specific threats requires: (1) precision chemistry (which is not scalable to detect arbitrary toxins), (2) dedicated sensors and hardware for each toxin (or analogues of the same toxin), and (3) a priori threat knowledge (e.g., one can only detect what the chosen sensor is designed to detect, so unexpected or unknown toxins/analogues cannot be detected). Furthermore, while canines are often effective, they (1) require extensive training and (2) expose the canine and handler to dangerous environments. "Electronic noses" are a powerful concept, yet current inceptions are inadequate (e.g., limited number and breadth of sensors on a chip, and they create a "data deluge" without embedded local processing of the data).

SUMMARY

In some aspects, a device includes a sensing layer that comprises a plurality of carbon nanotube field-effect transistors (CNFETs) functionalized with a set of functional materials to generate data based on at least a portion of a gas. Each CNFET of the plurality of CNFETs is functionalized with a functional material of the set of functional materials, and the set of functional materials includes at least 50 functional materials. The device also includes a memory layer, operably coupled to the sensing layer, to store the data generated by the plurality of CNFETs. The device also includes a processing layer, operably coupled to the memory layer, to identify one or more components of the gas based on the data generated by the plurality of CNFETs.

In some aspects, a method includes functionalizing a plurality of carbon nanotube field-effect transistors (CNFETs) functionalized with a set of functional materials. Each CNFET of the plurality of CNFETs is functionalized with a functional material of the set of functional materials, and the set of functional materials includes at least 50 functional materials. The method also includes coupling a memory layer to the sensing layer, to store data generated by the plurality of CNFETs. The method further includes coupling a processing layer to the memory layer to identify one or more components of a gas based on the data generated by the plurality of CNFETs.

In some aspects, a method includes diagnosing ventilator-associated pneumonia (VAP) and comprises culturing bacteria from a patient susceptible to VAP and detecting at least one volatile organic compound (VOC) emitted by the bacteria with a device. The device includes a sensing layer comprising a plurality of carbon nanotube field-effect transistors (CNFETs) functionalized with a set of functional materials for detecting at least one VOC. Each CNFET of the plurality of CNFETs is functionalized with a functional material of the set of functional materials, and the set of functional materials includes at least 50 functional materials. The device includes a memory layer operably coupled to the sensing layer, and a processing layer operably coupled to the memory layer. The method further includes diagnosing the patient as having VAP based on the at least one VOC.

In some aspects, a monolithic, three-dimensional (3D) integrated circuit (IC) includes a sensing layer that comprises a plurality of carbon nanotube field-effect transistors (CNFETs) functionalized with a set of functional materials for sensing a gas. The set of functional materials includes at least 50 functional materials. The device also includes a memory layer, operably coupled to the sensing layer, to store data generated by the plurality of CNFETs. The device further includes a processing layer, operably coupled to the memory layer, to identify the gas based on the data generated by the plurality of CNFETs.

In some aspects, a method of diagnosing ventilator-associated pneumonia (VAP) includes sensing an exhalation of a patient, and diagnosing the patient as having VAP based on the exhalation of the patient.

In some aspects, a system includes a ventilator to circulate air to a user, and a device coupled to the ventilator to receive air exhaled by the user. The device includes a sensing layer that comprises a plurality of carbon nanotube field-effect transistors (CNFETs) functionalized with a set of functional materials to generate data based on at least a portion of the gas. Each CNFET of the plurality of CNFETs is functionalized with a functional material of the set of functional materials, and the set of functional materials includes at least 50 functional materials. The device also includes a memory layer, operably coupled to the sensing layer, to store the data generated by the plurality of CNFETs. The device further includes a processing layer, operably coupled to the memory layer, to identify one or more components of the gas based on the data generated by the plurality of CNFETs.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 1 shows a schematic of a monolithic 3D smart sensing system, comprised of millions of unique carbon nanotube field-effect transistor (CNFET) gas sensors fabricated directly over memory and computing, all densely integrated through fine-grained and dense vertical interconnects. Due to the dense integration of massively parallel sensing, this system can capture terabytes of information each second and transform it to processed information (e.g., fentanyl classification) through embedded computing, which can still leverage silicon CMOS on the first layer.

FIG. 2 shows experimental data generated from a CNFET gas sensor array. Each pixel is the response of a single CNFET gas sensor (digitized to a binary value for clarity). The two patterns are the response from the CNFET gas sensor array when exposed to two different gases. The system classifies gases by matching previously learned patterns to measured patterns. Embedded learning predicts (with known uncertainty) if an unknown gas (or complex combination of gases) appears to be of the same "class" as a previously known gas (or complex combination of gases).

FIG. 3A shows an individual CNFET.

FIG. 3B shows a CNFET sensor with two CNFETs: the bottom CNFET is functionalized with conjugated molecules, transforming the bottom CNFET into a CNFET gas sensor. The dominant sensing mechanism is different gases interacting with the functional materials (e.g., conjugated molecules, and/or generally any material that coats the CNFET); this interaction modifies the functionalization-nanotube intermolecular forces, resulting in local changes in the electronic properties of the CNT, in turn resulting in changing CNFET drain current.

FIG. 4A shows a schematic of an individual Resistive Random Access Memory (RRAM) cell. RRAM is a non-volatile energy-efficient memory technology for dense on-chip data storage, and can be fabricated <200° C., and is therefore compatible with monolithic 3D integration.

FIG. 4B shows a sub-section of a 1 Mbit RRAM memory array.

Figure 6:
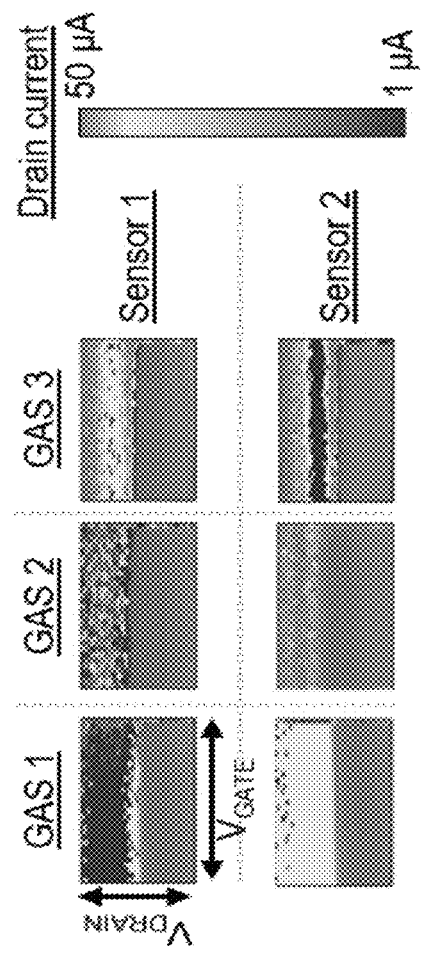

FIG. 6 illustrates CNFET gas sensor response patterns to different gases (columns) and different sensors (rows). Each pixel within each response pattern represents the CNFET drain current for a different biasing condition. The same sensor generates a unique response pattern for each gas, and CNFETs with different functionalizations respond with unique patterns. Therefore, thousands-to-millions of unique gas sensors, with each sensor capable of generating a unique pattern versus biasing condition, results in a massive hyper-dimensional sensing space.

Figures 7A, 7B, 7C, 7D:
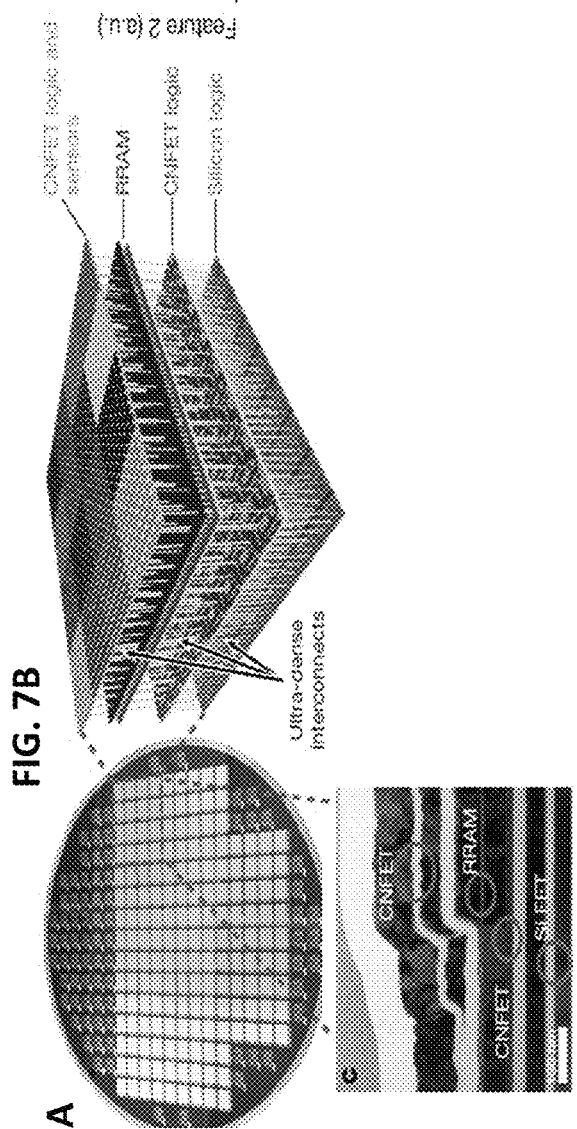

FIG. 7A shows a 100 mm wafer in which three-dimensional (3D) integrated circuits (ICs) have been fabricated.

FIG. 7B shows one of the 3D ICs fabricated in the wafer of FIG. 7A.

FIG. 7C shows a cross-sectional transmission electron microscope (TEM) image of a 3D IC (scale bar=100 nm).

FIG. 7D is a principle component analysis plot generated with raw data acquired by a 3D IC for vapors from different household liquids.

Figure 1:
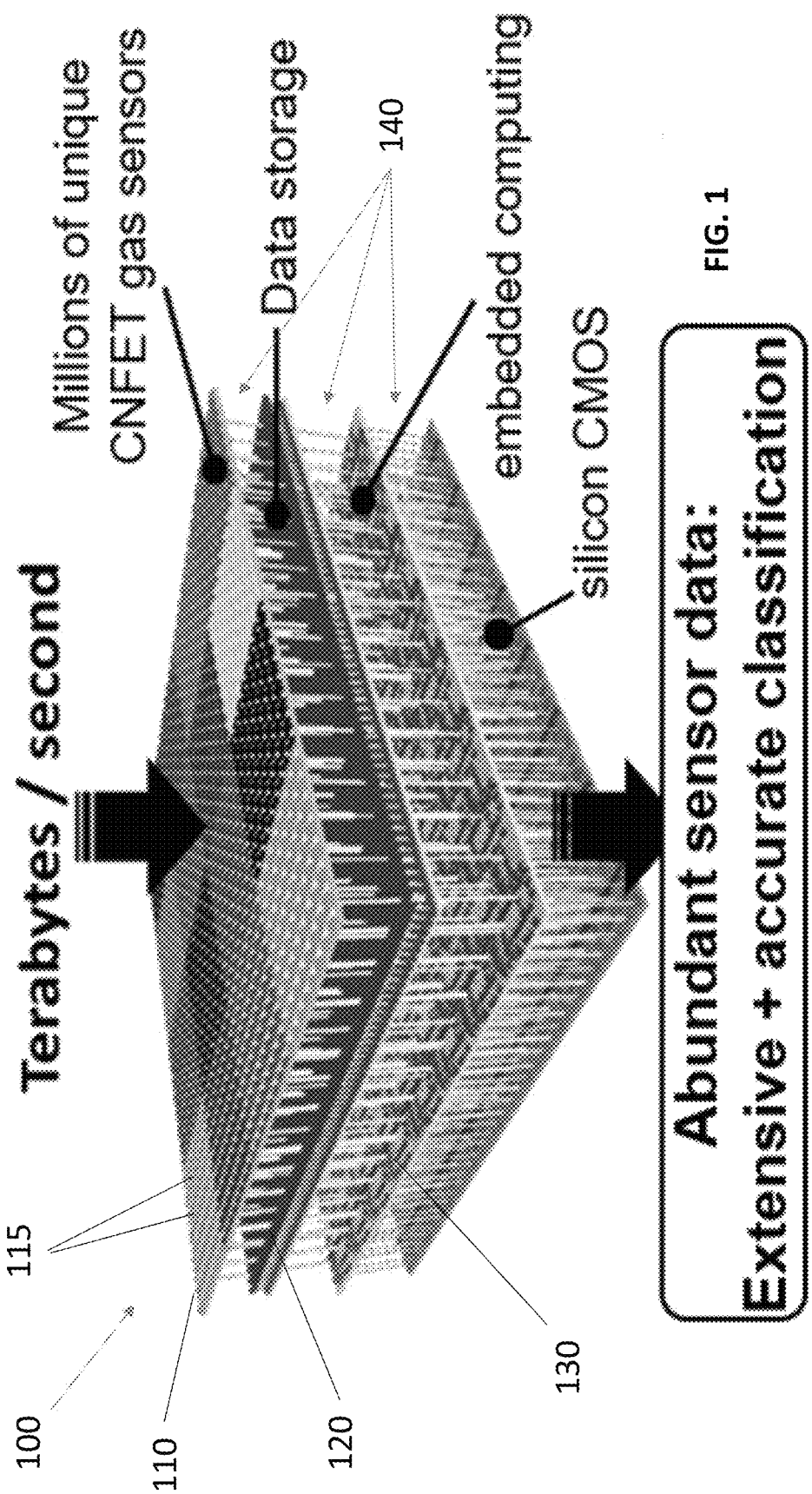
Figure 8:
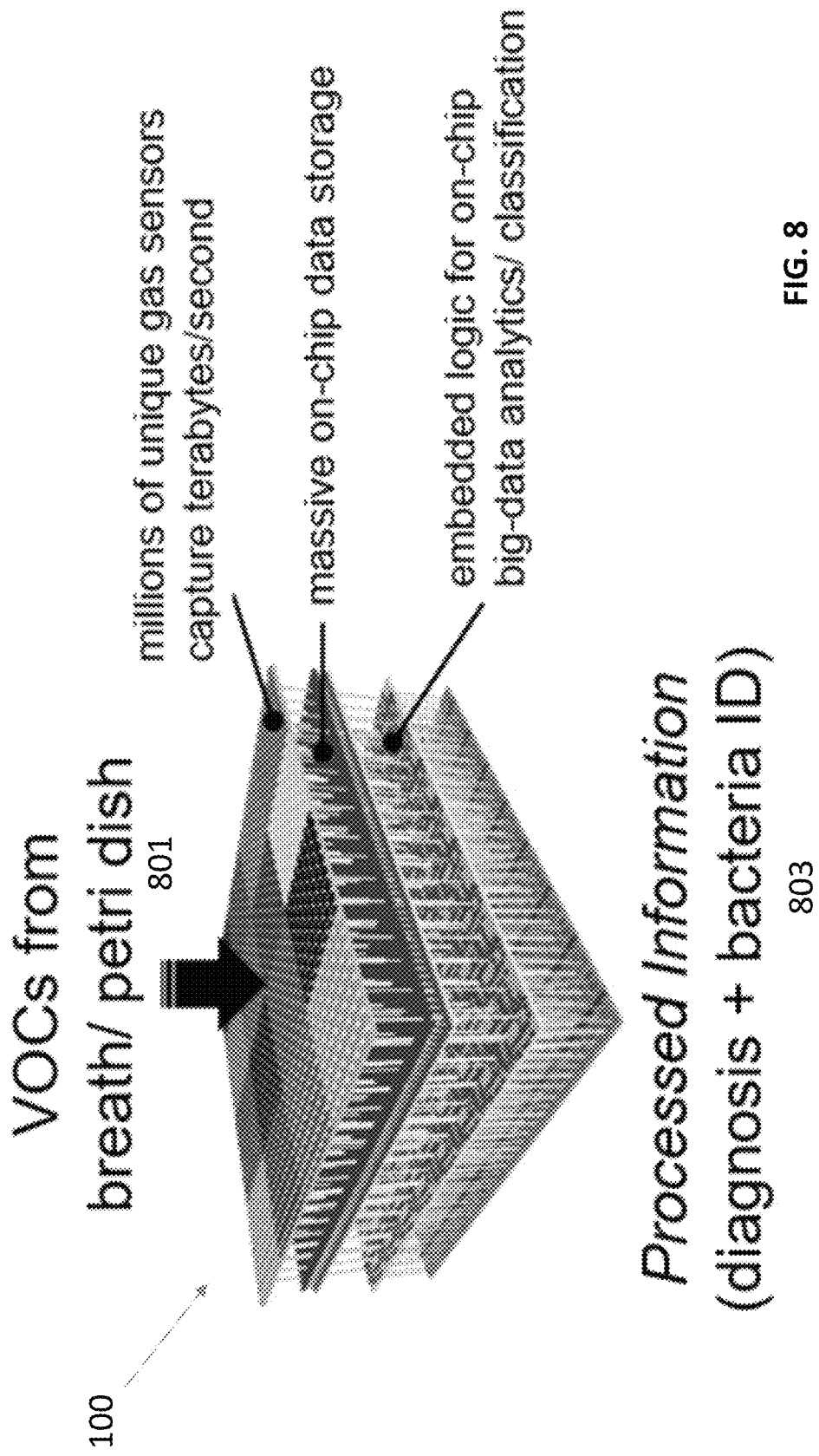

FIG. 8 shows the monolithic 3D smart sensing system of FIG. 1 configured as an electronic nose that detects volatile organic compounds (VOCs) in a patient's breath for diagnosing ventilator-assisted pneumonia (VAP).

Figure 9A:
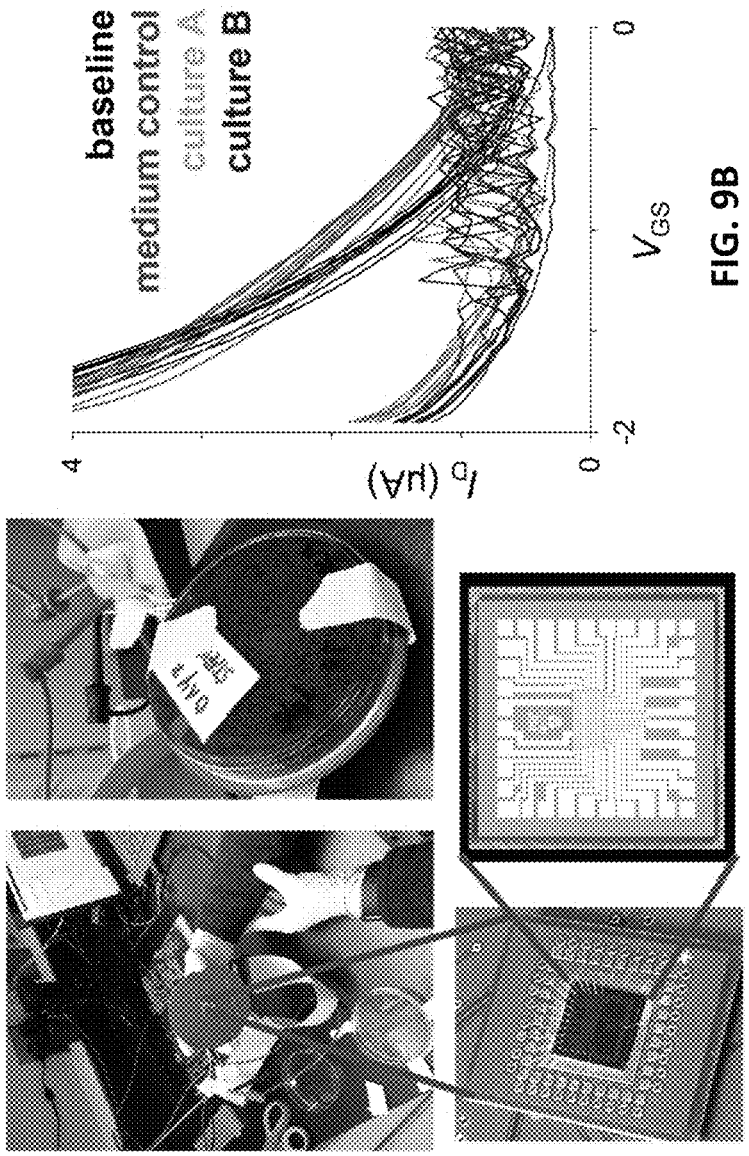

FIG. 9A shows an electronic nose integrated onto a Petri dish for detecting vapors from VOCs and other compound emitted by a bacterial culture grown in the Petri dish.

Figure 9B:
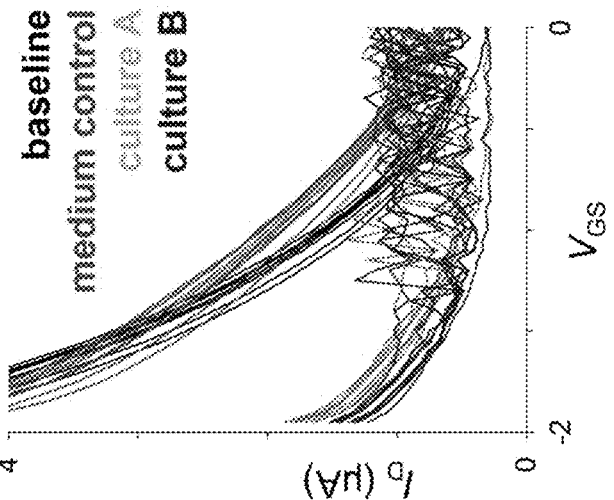

FIG. 9B is a plot of the electronic nose's response to a medium control and different cultures and a baseline response.

Figure 10:
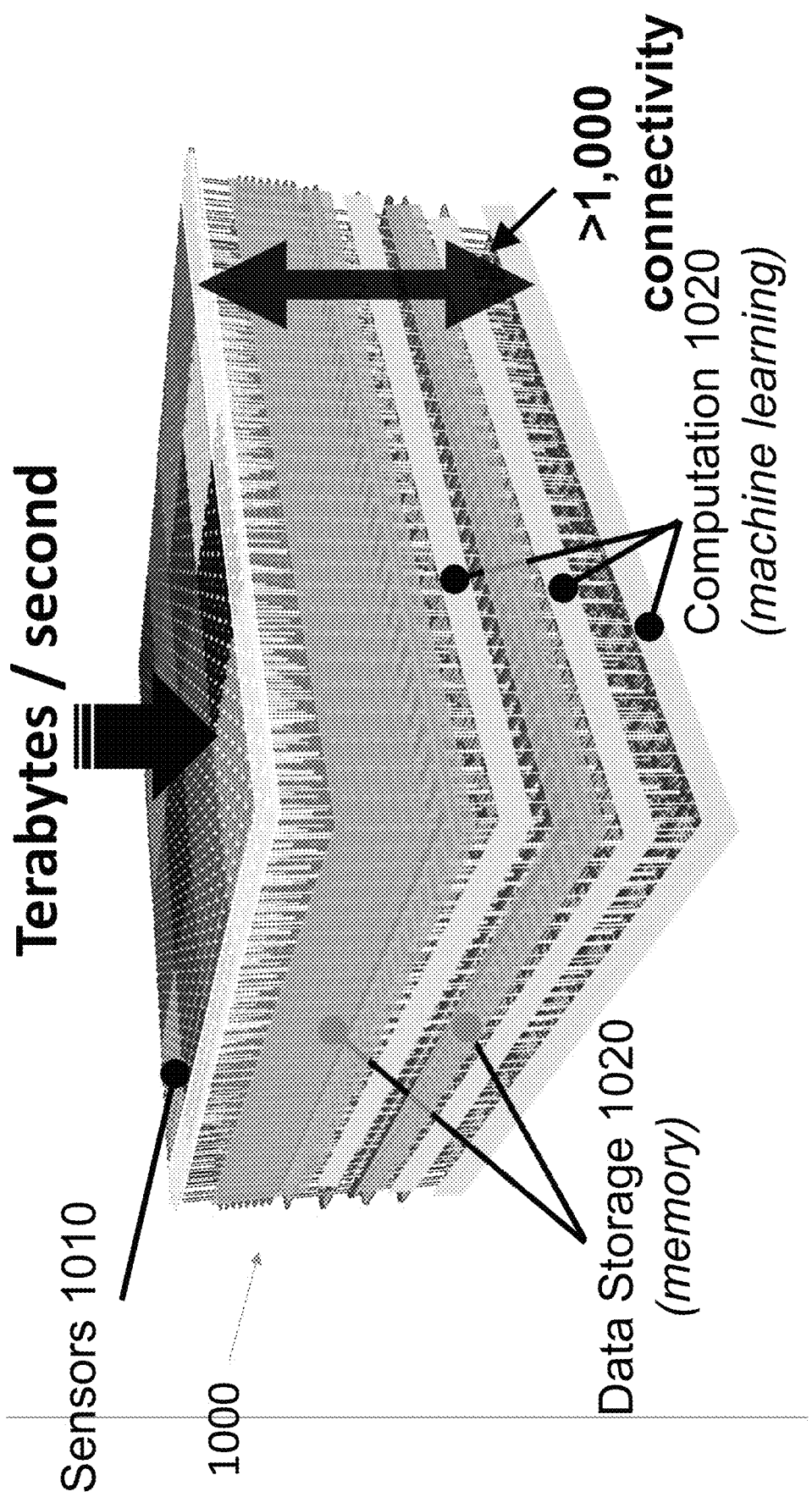

FIG. 10 shows an example monolithic 3D smart sensing system with multiple, stacked data storage and computation layers.

Figure 11:
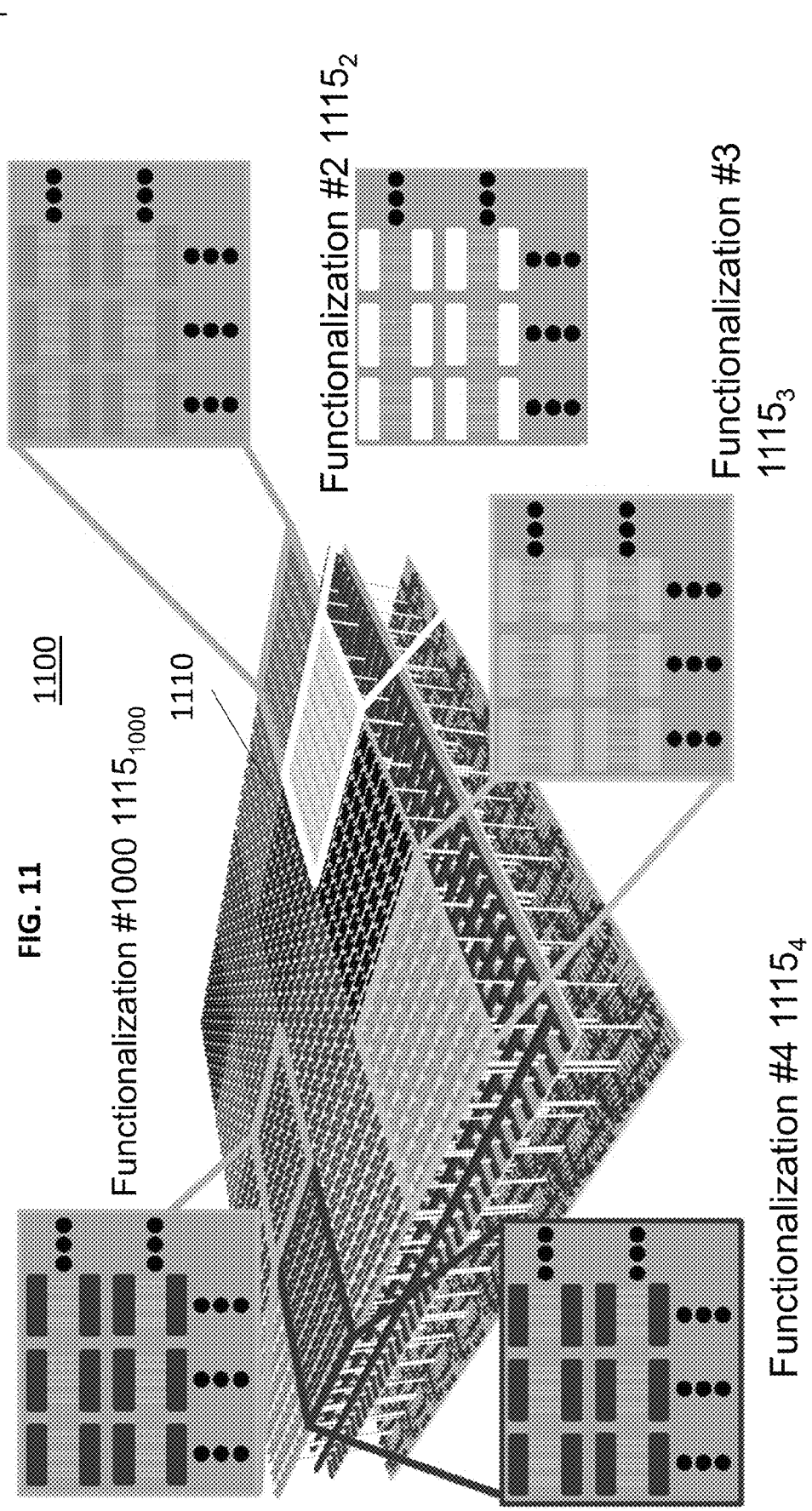

FIG. 11 shows an example monolithic 3D smart sensing system with multiple functionalizations in its CNFET subarrays.

Figure 12B:
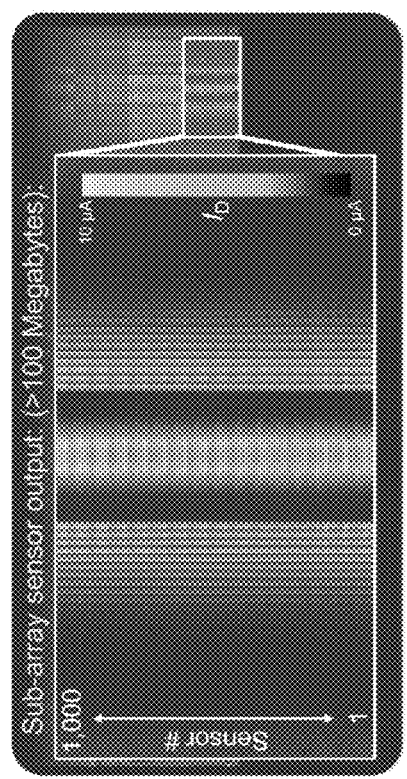
Figure 12C:
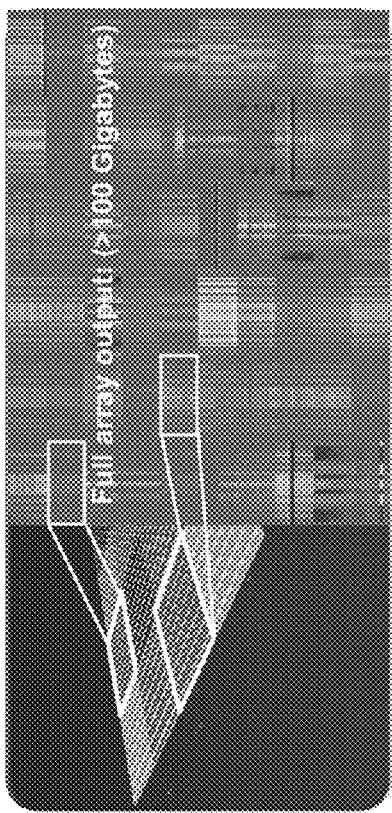
Figure 12A:
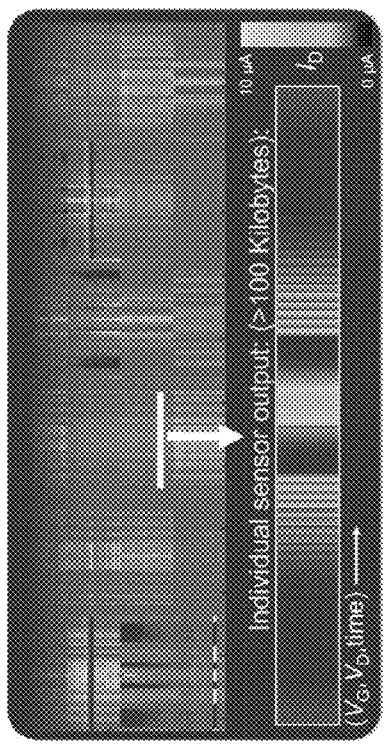

FIG. 12A illustrates an example current output of an individual CNFET gas sensor as drain voltage $V_D$ and gain voltage $V_G$ is varied in timing.

FIG. 12B illustrates an example output of a subarray of 1000 individual CNFET gas sensors, each of which has an output as generally illustrated in FIG. 12A.

FIG. 12C illustrates example output of an array of CNFET subarrays as illustrated in, and having outputs as generally illustrated in, FIG. 12B.

FIG. 13A is an example output of a CNFET subarray when exposed to air.

FIG. 13B is an example output of the CNFET subarray of FIG. 13A when exposed to air including a bacterial component.

FIG. 13C is an example output of the CNFET subarray of FIG. 13A when exposed to air including another bacterial component that is different from the bacteria component of FIG. 13B.

FIG. 13D is an output of an array of CNFETs when exposed to air in a headspace over a culture including the bacterium *Pseudomonas aeruginosa*.

FIG. 13E is an output of an array of CNFETs when exposed to air in a headspace over a culture including the bacterium *Staphylococcus aureus*.

FIG. 13F is an output of an array of CNFETs when exposed to air in a headspace over a culture including the bacterium *Haemophilus influenzae*.

Figure 14:
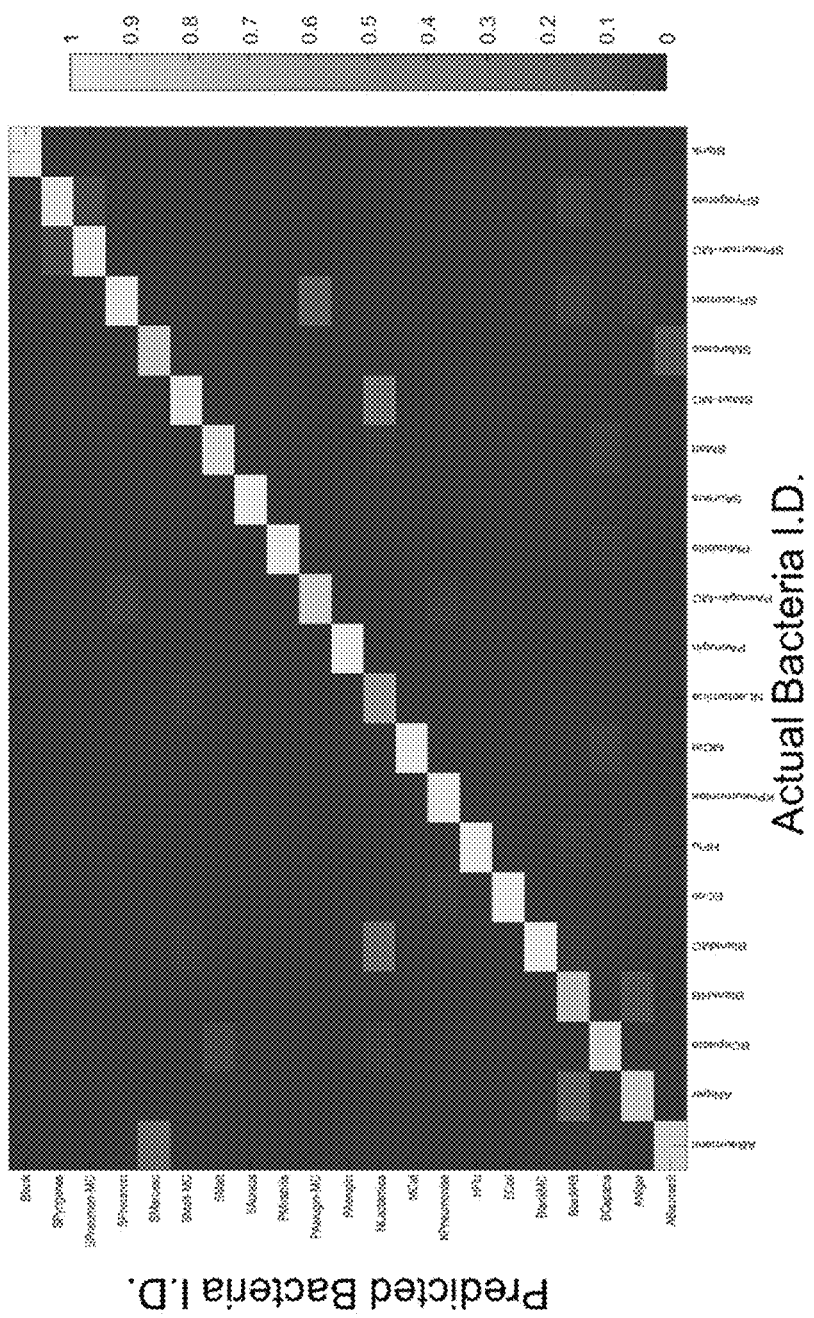

FIG. 14 is a plot of actual bacterium (X axis) that a CNFET array is exposed to versus the bacterium (Y axis) predicted/detected by the CNFET array. It illustrates the accuracy of a CNFET array in detecting different bacteria.

FIG. 15A illustrates an example device for gas sensing with different sub-systems/layers.

FIG. 15B illustrates operation of the device of FIG. 15A by interaction between its different sub-systems/layers.

FIG. 15C illustrates the phases of operation of the device of FIG. 15A.

Figure 16:
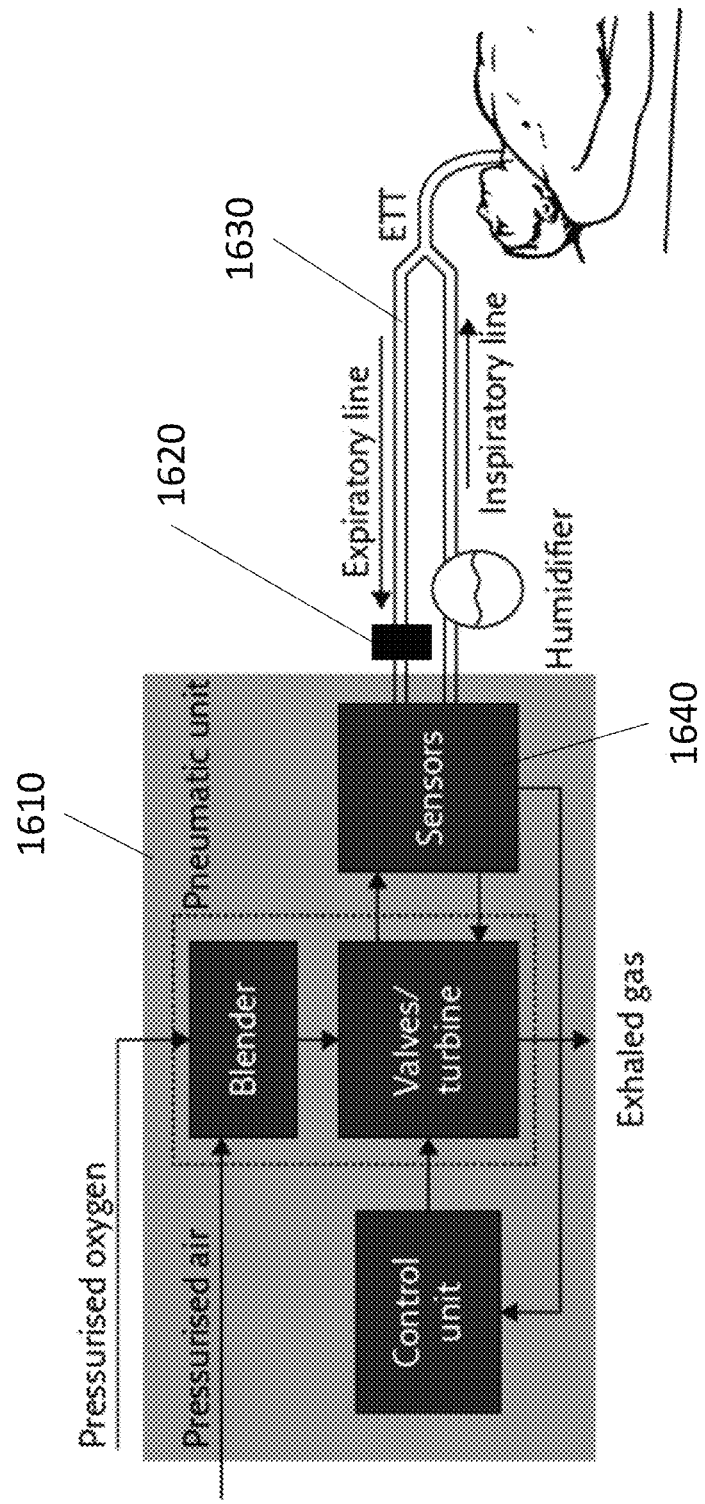

FIG. 16 illustrates a mechanical ventilator with a monolithic 3D IC disposed in an expiratory line.

DETAILED DESCRIPTION

The present technology includes smart sensing systems realized by integrating massive arrays of densely integrated and highly diverse on-chip sensors with embedded data storage and computation on the same chip, enabling a radically new "big-data" or "hyper-dimensional" approach to sensing applications. Other inventive smart sensing systems can be realized by chips with fabricated arrays of large numbers of highly diverse sensors and conventional readout circuitry and interconnects that read data off of the chips. These systems can be made by leveraging monolithic three-dimensional (3D) systems to integrate millions of unique on-chip gas sensors directly over layers of data storage and computation, achieving ultra-fine-grained integration of sensing, memory, and logic. Such systems are enabled by heterogeneously integrating multiple technologies within the same chip: conventional silicon CMOS and beyond-silicon emerging technologies (specifically Resistive Random Access Memory (RRAM) for non-volatile memory and carbon nanotubes (CNTs) for both energy-efficient embedded computation and diverse gas sensors). Such systems can transform terabytes of captured data from the outside world every second into "processed information" by performing in-situ classification of the sensor data using on-chip machine learning logic. This enables next-generation sensing applications by leveraging tightly integrated sensing with embedded computing for low-power on-chip classification and learning. For scalable fabrication, all of the sensors can be fabricated in an identical manner with the same material (e.g., carbon nanotubes), and these identical, "bare" sensors can then be made diverse, or unique, by functionalizing the sensors through any suitable high-throughput methodology (e.g., parallelized or serial (or any combination thereof) microspotting or spraying solutions containing different sensitive materials that coat the CNTs).

An example system can be realized as a mobile (e.g., handheld or wearable) smart sensing system trained to detect opioids from the fentanyl family (fentanyl and its analogues, both known and unknown). This can have profound implications for public health, health care providers, law enforcement, and homeland security. Such a chip can perform intelligent fentanyl detection and serve as a platform for a wide range of future smart sensing systems. For instance, the same hardware platform can be applied to healthcare, industrial and environmental monitoring, chemical warfare detection, hidden explosives or other hazardous threats, aerial gas sampling from unmanned aerial vehicles (UAVs), and other classes of sensors (e.g., high-speed imagers).

Massively Parallel Sensing Systems

FIG. 1 shows a sensing device/system platform 100, also sometimes referred to as a monolithic, three-dimensional (3D) integrated circuit (IC). The device 100 can include a sensing layer 110, a memory layer 120, and a processing layer 130. The ratio of sensing elements in the sensing layer 110, to memory elements in the memory layer 120, and/or to processing elements in the processing layer 130, can vary in any suitable manner such as, for example depending on the particular application (e.g., more compute-intensive applications may require more memory and processing, while less compute-intensive applications could include a sensing layer, and be without the memory, processing layers).

The sensing layer 110 can include carbon nanotube field-effect transistors (CNFETs) 115 that are functionalized. The number of CNFETs 115 in the sensing layer 110 can be about 100, about 1000, about 10,000, about 100,000, about 1,000,000, about 5,000,000, about 10,000,000 or more, including all values and sub-ranges in between. In some cases, the sensing layer 110 includes at least 1,000,000 CNFETs.

The functionalization can be with multiple functional materials and in any suitable manner. For example, the same functional material can be applied to some of the CNFETs 115, or multiple functional materials can be applied to a single CNFET 115, and/or the like. The multiple/set of functional materials can include any of the following classes of molecules and/or specific molecules: DNA such as oligonucleotides, metal coordination complexes, porphyrins including metal porphyrins, self-assembled monolayers (SAMs), polymers, pyrrole derivatives, phthalocyanines, combinations thereof, and/or the like. The set of functional materials can include at least 2, at least 4, at least 10, at least 20, at least 50, at least 100, at least 500 or more different functional materials, including all values and sub-ranges in between. Examples of functional materials can include, but are not limited to, 7-amino-4-(trifluoromethyl)coumarin, coumarin 153, 7-diethylamino-3-[N-(2-maleimidoethyl)carbamoyl]coumarin, anthracene, 7,12-dimethylbenz[a]anthracene solution, perylene, 9-anthracenemethanol, ethyl 2-methylpyridine-3-carboxylate, 1,4-diiodobenzene, 1-cyclohexene-1-carboxylic acid, biphenyl-4-carboxylic acid, biphenyl-2-carboxylic acid, 9-fluorenone-2-carboxylic acid, 1,6-dibromo-2-hydroxynaphthalene-3-carboxylic acid, 2-fluorobiphenyl-4-carboxylic acid, 6-methylpyridine-3-carboxylic acid, 3-bromopropylamine hydrobromide, 4-tritylphenol, 4-(phenylazo)benzoic acid, ethylene di(p-toluenesulfonate), tert-butyl indoline-1-carboxylate, β-cyclodextrin, (2-hydroxypropyl)-β-cyclodextrin, α-cyclodextrin, γ-cyclodextrin hydrate, dibenzo-18-crown-6, cesium tetraphenylborate, β-cyclodextrin hydrate, 2,6,8-trimethyl-quinoline-4-carboxylic acid, sodium dodecylbenzenesulfonate, 3-O-methyl-d-glucopyranose, ethylenediaminetetraacetic acid disodium magnesium salt hydrate, thymolphthalein, o-cresolphthalein complexone, biphenyl-4-methanol, 1-([1,1'-biphenyl]-4-yloxy)acetone, zinc phthalocyanine, magnesium phthalocyanine, aluminum phthalocyanine chloride, iron(ii) phthalocyanine, poly(copper phthalocyanine), copper phthalocyanine-3,4',4'',4'''-tetrasulfonic acid tetrasodium salt, nickel(ii) phthalocyanine-tetrasulfonic acid tetrasodium salt, copper(ii) 2,9,16,23-tetra-tert-butyl-29h,31h-phthalocyanine, hemin, 2-fluoro-5-methoxybenzaldehyde, phenazine methosulfate, 2-(4-(isopentyloxy)-3-methoxyphenyl)-1h-imidazo(4,5-b) phenazine, brilliant cresyl blue, brilliant green, tricyclohexylphosphine tetrafluoroborate, thionin acetate salt, 1,3,7-trimethylxanthine, nafion 1100ew, poly(ethyleneimine), sulfanilic acid, 2-(3,4'-dimethoxyphenyl)-1-(3''-pyridinyl)acrylonitrile, and 2-[bis(methylthio)methylene]malononitrile. In some cases, the deposition of the functionalization materials can be done by automated microspotting or spraying over different areas of the sensing layer 110 (e.g., with positional accuracy of <100 μm in any direction), by pre-alignment of the device 110 to a microspotter or sprayer, e.g., optically or through other automated means. The device 100 can further include, at during fabrication and/or after, structures or patterns that confine functionalization materials or solutions containing functionalization materials within the targeted areas of the device (e.g., such as within a 500 μm×500 μm area or smaller). This confinement can be through, for example, physical wells fabricated surrounding groups of CNFETs, or through patterning materials with different hydrophobicity on the surface of the sensing layer 110 to confine solutions containing the functionalization material(s) within specific regions of the sensing layer 110 until the solution dries.

When exposed to a gas, or a portion/component thereof, each CNFET 115 in the sensing layer 110 can respond based on its specific functionalization to generate data/information for that gas, as described in more detail herein. For example, in some cases, the functionalization can be specific for a particular gas, and the data generated by that CNFET 115 is indicative of the presence or absence of that particular gas. In other cases, the functionalization is not specific for a particular gas, and the data generated by that CNFET 115 in response to that gas, along with the data generated by other CNFETs with different functionalization, is collectively indicative of the presence or absence of that particular gas. Said another way, a first CNFET 115 can be functionalized to sense a first type of gas, a second CNFET 115 can be functionalized to sense a second type of gas, and so on.

The memory layer 120 is coupled to the sensing layer 110 and can include any suitable storage components for storing the data generated by the CNFETs 115 such as, for example, RRAMs, embedded Flash (eFlash) memory, phase-change memory (PCM), SRAM, magnetic and/or spin-based memories such as spin-transfer torque RAM (STT-RAM). Multiple inter-layer vias (ILVs) 140 can couple the layers 110, 120. The memory layer 120 can encompass a cross-point architecture, with each cell including one transistor and one memory unit, such as an RRAM.

The processing layer 130 is coupled to the memory layer 120 and can include any suitable processing components for identifying one or more components of the gas based on the data generated by the CNFETs 115, for identifying a response of the CNFETs 115 to one or more components of the gas, and/or the like. In some cases, the gas includes fentanyl, and the device 100 (i.e., the functionalized CNFETs 115) can collectively detect fentanyl. In some cases, the gas includes volatile organic compounds (VOCs), and the functionalized CNFETs 115 can detect one or more of the VOCs in the gas. The VOCs can include, but are not limited to, VOCs released from bacteria, VOCs released from a (human or non-human) patient's own cells and/or biological processes, VOCs that could be released from an agent external to the bacteria or the patient, e.g., administered to a bacterial culture or to the patient. Generally, the CNFETs 115 can produce a unique overall response to the gas, the memory layer 120 can store that a representation of that unique response, and the processing layer 130 can identify the gas based on the unique response.

Without being limited by theory or any particular implementation, the device 100 can integrate massively parallel sensing (i.e., via the CFNETs 115 in the sensing layer 110), data storage (i.e., via the memory layer 120), and computing (i.e., via the processing layer 130), such as, for example, for implementing look-up tables (LUTs), for pattern matching, and/or for embedded machine learning using any suitable supervised learning approach such as, but not limited to, support vector machines (SVMs), artificial neural networks, decision trees, random forests, and/or the like. It can be trained to detect fentanyl (and its unknown analogues), performing on-chip real-time classification.

Figure 2:
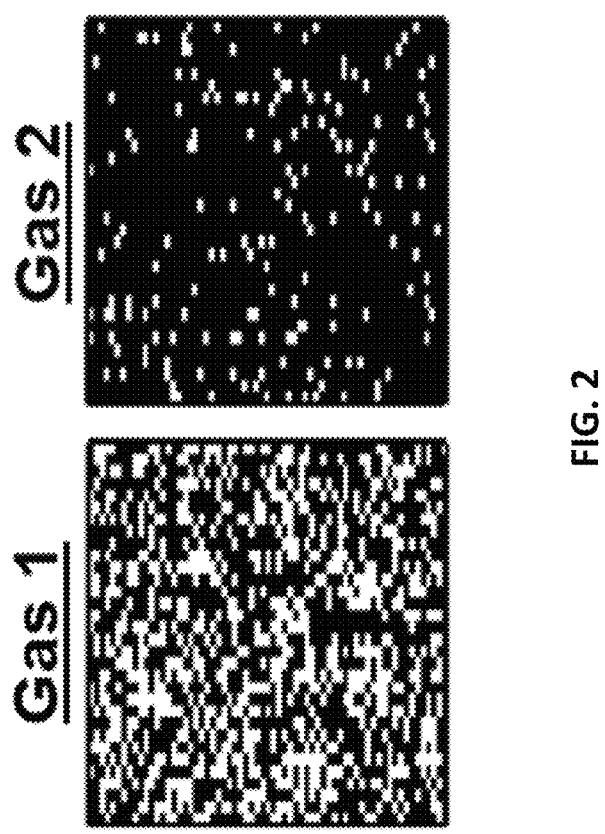

The platform/device 100 includes a chip whose top layer, which is exposed to the environment, can contain millions of unique gas sensors to generate rich sensing data. Classifying toxins can be based on the overall response of the millions of sensors, with each different toxin generating a unique response pattern across all millions of sensors, i.e., a unique identifying "fingerprint," as shown in FIG. 2 for a hypothetical Gas 1 (left panel) and Gas 2 (right panel). As a result, the accuracy requirements on each individual CNFET/sensor can be greatly relaxed, as sensing accuracy can come from the collection of sensors in the sensing layer 110 as a whole.

Performing classification based on unique patterns of responses from gas sensors can enable at least three benefits: (1) flexibility and generality: the same device/hardware can be used to detect a wide variety of gases, substances, toxins, etc. simply by training new fingerprints or response patterns; (2) specificity: the unique fingerprint response allows the system to recognize specific toxins and/or classes of toxins, without requiring specifically-engineered sensors for that toxin or class or toxins; and (3) robustness, since hundreds, thousands, tens of thousands, hundreds of thousands, or millions of sensors provide robustness to stray responses from individual sensors.

However, simply having millions of sensors without functionalization or without parallel readout can be insufficient: the exponentially increasing amount of generated raw data from sensing systems (i.e., the "data deluge") already overwhelms computing capabilities of electronics. Transferring data off-chip to the cloud, or even between two individually packaged chips, can result in prohibitive communication bottlenecks that waste both time and energy, often consuming >98% of the time and energy of the total classification operation. (This quantification is extracted from simulations of example 2D vs. 3D systems, calibrated to performance and energy numbers extracted from full physical designs and industry-standard design flows.) This is particularly constraining for hyper-dimensional approaches to sensing due to the reliance on massive amounts of generated raw data and subsequent big-data analysis.

To alleviate this problem, and as described for the device 100, the on-chip sensors/CNFETs 115 are immersed within memory (in the memory layer 120) and computation (in the processing layer 130), transforming the raw data deluge into highly processed information all on-chip/on-device, before being transmitted off-chip, thus overcoming this substantial communication bottleneck. As shown in FIG. 1, this is accomplished through heterogeneous integration of layers of logic, memory, and sensing directly over one-another within a 3D stack, with the layers connected through fine-grained and dense vertical vias. A single 3D stack may include any number of logic, memory, or sensing layers (e.g., multiple sensing layers connected to a single memory layer and a single logic layer). This provides massive sensing capabilities unattainable today through any other approaches.

Methods of Manufacture—CNTs, RRAM, and Monolithic 3D Integration

As a non-limiting description, the device 100 can be manufactured by functionalizing multiple carbon nanotube field-effect transistors (CNFETs), such as the CNFETs 115 in the sensing layer 110, with a set of functional materials. Each CNFET can be functionalized with one or more functional materials (e.g., at least 50 functional materials). In some cases, this can be done by depositing carbon nanotubes on a substrate, then functionalizing the carbon nanotubes with the set of functional materials. Then the rest of the CNFET can be constructed to provide functionalized CNFETs, such as by depositing materials to form the source and the drain terminals, by appropriate deposition of additional materials. The functionalization itself, whether performed on carbon nanotubes prior to CNFET formation or after can be done by, for example, dropping a solution including the functional material on target carbon nanotubes. As another example, such as when a larger exposure area is desired, an aerosol solution that includes the functional material can be sprayed onto the target carbon nanotubes.

The memory layer 120 can be coupled to the sensing layer 110, such as through ILVs 140, which enables the memory layer 120 to store the data generated by the CNFETs 115 in response to gas exposure. The processing layer 130 can then be coupled to the memory layer 120, which permits the identification of one or more components (e.g., fentanyl, VOCs, etc.) in the gas based on the data from the CNFETs 115. Accordingly, during use, the CNFETs 115 can be exposed to the gas, such that they generate the data based on at least a portion of the gas. Then processing layer 130 can the identify the one or more components of the gas based on the data.

As a specific and non-limiting example, the example device/system 100 shown in FIG. 1 can be fabricated using CNTs, RRAM, and monolithic 3D integration. A CNT is a nano-cylinder of carbon atoms with a diameter of about 1 conjugated materials results in an equally massive design space for unique CNFET gas sensors. Moreover, owing to high drive currents of CNFETs simultaneously with ideal electrostatic control, CNFETs can realize energy-efficient computing with more than 10 times the energy efficiency (quantified by the energy-delay product, or EDP) at the circuit-level compared to state-of-the-art silicon CMOS transistors. Finally, CNFETs can be fabricated at very low temperatures (e.g., <200° C.), which enables dense 3D integration between vertical layers of sensing and computing (discussed below).

Nevertheless, CNT sensors present some challenges, including those listed in the table below. Those challenges can be mitigated as follows:

| Challenge | Realizing thousands to millions of diverse CNT gas sensors | Method for functionalizing arrays of CNT sensors | Characterizing thousand-to-millions of diverse CNT gas sensors | Sensor spoiling (e.g., ensuring reversible operation) |
|---|---|---|---|---|
| Solution | Functionalize CNTs with unique combinations of hundreds-to-thousands of commercially available functionalization materials (demonstrated experimentally) | Automated high-throughput micro-spotting (commercially available) | Leverage same monolithic 3D ICs with ultra-high-bandwidth for rapid sensor characterization | Massive sensor space allows on-chip learning to weigh sensors that recover more efficiently in a given ambient; sensor development will work to overcome these effects. system-on-chip enables low-cost, potential for single-use chips. | nm. They can be used to form carbon nanotube field-effect transistors (CNFETs) by replacing the silicon channel of a transistor with CNTs. CNFETs provide several benefits for smart sensing systems. First, as shown in FIGS. 3A (CNFET) and 3B (CNFET sensor), otherwise identical CNFETs can be transformed with different functionalizations to form a diverse set of unique gas CFNET sensors. To form a CNFET gas sensor 310, CNTs 320 in the channel of the CNFET 310 are functionalized (e.g., coated) with another material 330, though it is understood that any area of the CNFET, such as the source and drain contacts, can be functionalized with a coating of a functionalization material. For CNTs, this functionalization and its interaction with the CNTs 320 alters the behavior of the CNFET 310, thus determining its sensitivity and selectivity as a sensor. The thousands to millions of CNFETs in a single system can include many groups of CNFETs, each of which is functionalized to detect a specific gas or combination of gases, making it possible to sense different gases and combinations of gases with the same system.

CNTs can be modified with a wide range of functionalities. Specifically, due to the conjugated pi systems (alternating single and double bonds) present in CNTs, the functionalization materials as disclosed herein can interact with the nanotubes and influence their electronic structure such that when the functionalization material interacts with gas(es), any changes in the functionalization material are transduced into changes into the CNFET electrical properties, that are in turn observable by changes in the CNFET operation. Examples of such changes can include changes in the D.C. current-voltage relationships (drain current vs. drain voltage, and drain current vs. gate voltage), changes in A.C. response, transient response, impedance at different frequencies, combinations thereof, and/or the like. Generally, interactions of these functionalization materials with gas analytes of interest lead to direct changes in the electronic behavior of the CNTs—sensitizing each sensor to specific classes of gases. The massive number of available RRAM, shown in FIGS. 4A (single RRRAM cell) and 4B (RRAM array of RRAM cells), is a non-volatile memory technology for dense on-chip data storage. Similar to CNFETs, RRAM can also be fabricated at low (e.g., <200° C.) processing temperatures, and thus enables dense 3D integration, though any memory that can be fabricated under similar conditions (e.g., at temperatures of less than about 400° C.) can be employed.

Figure 5:
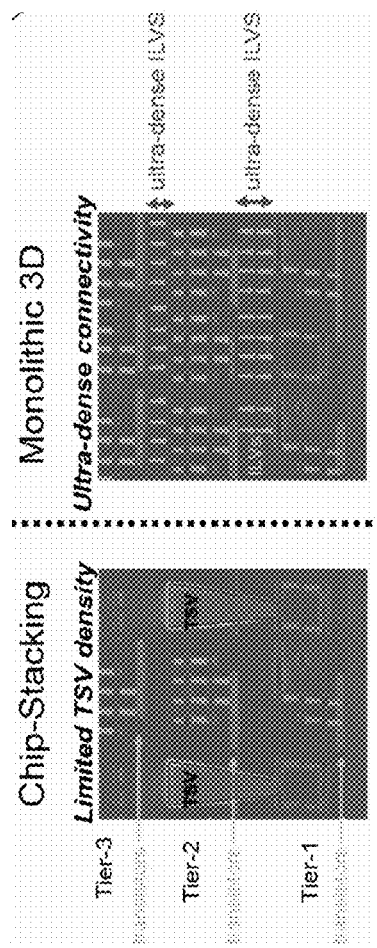
FIG. 5 shows chip-stacking (left), with sparse through-silicon vias (TSVs) connecting vertical layers, vs. monolithic 3D (right), with ultra-dense inter-layer vias (ILVs) connecting vertical layers. Monolithic 3D is naturally enabled by using CNFETs and RRAM for upper layers of memory, logic, and sensing, due to their low temperature fabrication.

Monolithic 3D integration can reduce or eliminate the communication bottleneck in transferring massive amounts of data between disparate parts of conventional sensing applications. An example device/system 100 as described herein with respect to FIG. 1 uses CNFETs and RRAM in a monolithic 3D system architecture to overcome this bottleneck. In contrast, conventional 3D integration today is achieved through chip-stacking, where each vertical layer of the system is fabricated on separate substrates, which are then stacked and bonded over one-another. However, chip-stacking typically relies on low-density through-silicon vias (TSVs) to connect vertical layers. TSVs are limited to >10 μm pitch as shown in the left panel in FIG. 5. Conversely, monolithic 3D integration involves fabricating each vertical layer directly over the previous layers. These layers are on the same starting substrate (no wafer bonding required), so that back-end-of-line inter-layer-vias (ILVs) used already for metal routing can be used to connect vertical layers. ILVs are orders of magnitude (e.g., more than 1,000 times) denser than TSVs, enabling higher density, as illustrated in the right panel in FIG. 5.

This massive increase in vertical physical connectivity translates directly into an equally large increase in data bandwidth between vertical layers. This enables massive numbers of diverse sensors (e.g., CNFET sensors with different functionalizations) to write their data in parallel to layers of memory, which are physically located directly underneath the sensors. Then, the data in memory is transferred to processing elements (directly beneath the memory) with equally high bandwidth, enabling highly processed information with low latency, e.g., for classification of massive sensor data in real time.

To realize monolithic 3D ICs, the processing temperature on the upper-layers can be less than about 400° C. Higher temperatures than this can damage bottom-layer circuits and destroy back-end-of-line metallic interconnects. While conventional silicon CMOS involves processing temperatures of >1000° C., which is too high for monolithic 3D ICs, the low-temperature fabrication of CNFETs and RRAM naturally enable monolithic 3D integrated circuits (ICs). This combination of sensing, data storage, and computing technologies, as well as the monolithic 3D system architectures, enabling the inventive smart sensing systems.

The abilities to capture massive and rich raw data and to process the data in near real-time on-chip provide additional opportunities for "smart" data analysis. For example, an example smart system may use massive real-time data input streams to perform adaptive data acquisition and subsequent machine learning. In FIG. 6, not only do two CNFET sensors ("Sensor 1" and "Sensor 2") with different functionalization provide unique responses to different gases ("Gas 1", "Gas 2", and "Gas 3"), the same CNFET sensor can provide different responses to gases when the CNFET is biased at different voltages (not shown). While a naïve approach to hyper-dimensional sensing may involve sampling across this entire vast space (across all biasing conditions across all sensors), an inventive system performs a real-time analysis on the captured data, making it possible to leverage previously measured responses to modify what data is collected from each of the sensors in the next measurement (by modifying the biasing conditions). Therefore, rather than sweeping across all possible biasing conditions for all sensors, the system can autonomously adapt in real-time (e.g., stop sampling sensors which are not providing useful information to save energy and time, while simultaneously increasing sampling from sensors gathering useful information).

Monolithic 3D ICs present challenges as well. For example, fabrication yield tends to decrease with each additional vertical layer. But sensing with hyper-dimensional data is generally robust to errors, and error-sensitive computing can be implemented with foundry silicon CMOS on the bottom layer. Likewise, thermal constraints can be mitigated by placing heat-generating layers, such as computing layers, at or towards the bottom of the IC next to heat-sink, and using upper layers for sensing, memory, and other tasks that generate (and dissipate) less heat.

Detecting Fentanyl

Current approaches for fentanyl (and broadly gas) detection have major limitations. Mass spectrometry does not yield sufficient information for identifying complex gas mixtures and must be used with gas chromatography (which is bulky and not mobile) for accurate gas identification. Moreover, mass spectroscopy fundamentally has lower resolution and sensitivity at smaller scales (e.g., on-chip). Several commercial fentanyl detectors use Raman spectroscopy, yet suffer from low signal intensity and thus cannot identify trace gases in ambient air.

While functionalization materials can be deposited over any component of a CNFET, CNTs can are particularly useful as extremely sensitive gas sensors. Due to their extreme electrostatic sensitivity and remarkably high surface-area-to-volume ratio (>10,000), functionalized CNT gas sensors have demonstrated part-per-billion (ppb) and even to part-per-trillion (ppt) sensitivity for a wide range of different analytes. However, functionalizing the CNTs prior to depositing the CNTs on a wafer/substrate and subsequent CNFET fabrication (e.g., of source, drain, or gate of the CNFET) have been used in highly specific and sensitive sensors, which is not a scalable approach for generalized smart sensing systems (as discussed above). Moreover, often these functionalization materials are considered chemical contaminants in semiconductor manufacturing facilities, and thus subsequent fabrication of the CNFET sensor post-CNT functionalization can be challenging, as the functionalization of the CNT prohibits continued fabrication within semiconductor fabrication facilities. Arrays of CNTs have been used in non-specific sensors for identifying different vapors. However, these devices have used a severely limited number of sensors (e.g., 3 to 30), thus also use a limited number of different types of sensors, and have also been packaged on separate chips from memory and compute.

FIGS. 7A-7D show an example large-scale, monolithic 3D IC with >1 million CNFET gas sensors and 1 Mbit of RRAM fabricated over silicon CMOS logic. It implements support-vector machine for classification and leverages a few different CNFET functionalizations to detect household vapors. This IC is controlled externally from a computer.

Other example ICs may implement sophisticated on-chip learning and classification with advanced silicon CMOS logic on the bottom layer. They may leverage micro-spotting and/or aerosol-based spraying/deposition to achieve >100,000 unique functionalizations across the array, including functionalizations for a variety of applications, including as fentanyl detection, healthcare, industrial monitoring, etc. And they may operate as autonomous, low-power, and mobile smart sensing systems that implement real-time, hyper-dimensional adaptive data capture and analysis.

For instance, an inventive monolithic 3D IC sensing system may include any of a variety of unique CNT gas sensors in over different gas combinations and concentrations, including trace (<100 ppm) fentanyl detection in a range of ambient conditions (humidity, background gases, etc.). In operation, these monolithic 3D ICs may be capable of learning unknown analogues with target sensitivities of ~1 ppm trace concentrations in ambient conditions. These CNT gas sensors may form a library with different known pattern responses to fentanyl analogues. This library can be used for off-line testing and optimization of CNT sensors with experimental data, thereby reducing risks associated with optimizing embedded computing for identifying and predicting unknown fentanyl analogues. Said more generally, these CNT gas sensors are collectively able to continuously learn patterns, even when exposed to unknown gases, and without reengineering to detect new gases. Additionally, these CNT gas sensors are also collectively able to classify an unknown molecule as being related or unrelated to fentanyl based on the collective response from all sensors.

Detecting Volatile Organic Compounds for Diagnosing Ventilator-Assisted Pneumonia Ventilator-associated pneumonia (VAP) is a high-mortality illness that affects about 18% of Intensive Care Unit (ICU) patients within 15 days of intubation. It is associated with a direct cost of $10,000 to $15,000 and hospital stay increase of more than six days. Early detection of VAP is essential, as early antibiotic treatment lowers mortality and overall cost. Unfortunately, VAP diagnosis is extremely challenging due to: (1) the non-specificity of symptoms (elevated white blood cell count, fever), (2) the high false positive rate of respiratory tract cultures (and the required culture time), and (3) the lower utility of X-ray imaging in the ICU as chest infiltrate abnormalities are common in intubated patients, even without the presence of pneumonia.

Recent studies in VAP have found correlations between VAP and the composition of volatile organic compounds (VOCs) present in breath. Thus, changes in VOCs (both composition and concentration) can be used as markers of VAP status and response to treatment. While these results are extremely promising, it is infeasible to implement VOC monitoring of ICU patients for early VAP diagnosis with todays' technologies. Current techniques are both too bulky and expensive (e.g., state-of-the-art gas chromatography and mass spectrometry) to implement at scale, or inadequate for detecting VAP as they do not generate enough useful data (e.g., only contain <30 different sensors for detecting <30 specific VOCs). There are thousands of different VOCs in the breath, and there is no direct correlation with any specific VOC to the diagnosis of VAP (particularly since VAP itself is not a well-defined disease and can be caused by a range of different bacteria, each different bacteria can generate a unique VOC signature, and different people can have different responses to VAP).

FIG. 8 shows the monolithic, 3D IC 100 of FIG. 1 configured as an "electronic nose" that monitors VOCs 801 in patient breath for the early diagnosis of VAP. As explained above, the monolithic, 3D IC 100 may include millions of unique gas sensors built directly over layers of data storage and computing logic as explained above. Due to the fine-grained and dense integration of computing, data storage, and massively parallel sensing, these systems can capture terabytes of information each second, store that data in on-chip memory, and compute on it in real-time, transforming massive raw data input into highly-processed and useful information. Therefore, rather than determining *a priori* which VOCs to monitor for VAP diagnosis (which as mentioned above is infeasible), this multi-million sensor sensing system generates a unique response to arbitrary combinations and concentrations of VOCs.

Thus, rather than measuring individual VOC concentrations, an electronic nose can generate and perform the subsequent analysis of big-data from a given patient's breath to create a unique, personalized "fingerprint" 803 correlated to the entire composition of that patient's breath. The computing logic within the chip trains to recognize this personalized baseline, and detects changes in this "fingerprint" over time, including changes indicative of VAP. Therefore, training on the massive data sets generated by these systems (and knowing which patients developed VAP and which did not) makes it possible to recognize changes in the "fingerprints" which are indicative of VAP developing (without knowing exactly what these warning signs are), allowing clinical intervention. Likewise, monitoring VOCs in a patient's breath with an electronic nose provides information about the effectiveness of antibiotic treatment based on the rate at which the fingerprint returns to the patient's unique baseline.

A monolithic, 3D IC for diagnosing VAP may be realized by integrating massive arrays of densely integrated and highly diverse on-chip sensors with embedded data storage and computation on the same chip, enabling a radically new "big-data" or "hyper-dimensional" approach to sensing applications. Specifically, these systems can be made by leveraging monolithic 3D systems to integrate millions of unique on-chip gas sensors directly over layers of data storage and computation, achieving ultra-fine-grained integration of sensing, memory, and logic. Such systems are enabled by heterogeneously integrating multiple technologies within the same chip: conventional silicon CMOS and beyond-silicon emerging technologies (specifically RRAM for non-volatile memory and CNTs for both energy-efficient embedded computation and diverse gas sensing). Such systems can transform terabytes of captured data from the outside world every second into "processed information" by performing in-situ classification of the sensor data using on-chip machine learning logic. This enables next-generation sensing applications by leveraging tightly integrated sensing with embedded computing for low-power on-chip classification and learning.

FIG. 9A shows an electronic nose integrated onto a Petri dish for detecting vapors from VOCs and other compound emitted by a bacterial culture grown in the Petri dish. The monolithic 3D IC is integrated into the Petri dish to measure VOCs from a bacterial culture grown in the Petri dish. Such a bacterial culture study can result in immediate clinical impact.

Current diagnostic workflows to detect the presence and identify bacterial infections require several days to manually culture sufficient bacteria for testing. Recent work indicates that in culture, different bacterial strains can be identified from their released VOCs, and that the presence of these VOCs are generated prior to visible colonization (which is required in current diagnostic workflows). Compared to current diagnostic workflows, electronically detecting the presence of bacteria and identifying the bacteria strain based on VOCs decreases the time required to detect and identify bacterial infection, and thus the time to treatment with appropriate antibiotics, improving clinical outcomes for a wide range of bacterial infections.

FIG. 9B is a plot of the electronic nose's response to different cultures in the form of drain current versus gate-source voltage for the CNFETs in the monolithic, 3D IC. The steeper traces, which fall from a drain current of about 4 µA to about 0.5 µA with a gate-source voltage increase from −2 V to 0 V, correspond to the baseline response and to the response to a medium control. The shallower traces, which fall from a drain current of about 1-2 µA to about 0.5-1.0 µA with a gate-source voltage increase from −2 V to 0 V, correspond to responses to different bacteria cultures A (*E. coli*) and B (*P. aeruginosa*). The difference in the electronic nose's responses makes it straightforward to distinguish the bacteria cultures from the control.

While explained herein with respect to bacterial detection in a host of settings (ventilators, petri dishes, samples from patients, etc.), it is understood that the detection can be useful for detecting gases from non-bacterial species as well such as, for example, fungus/fungal infections that generate VOCs.

In addition, the Petri dish measurements yield massive datasets that can be used for training monolithic 3D ICs to recognize distinct patterns resulting from different bacteria. This training data can be leveraged for VOC detection and VAP diagnosis by a trained 3D IC that measures a ventilated patient's breath in situ. Diagnosing VAP in situ would dramatically reduce, if not eliminate, the lag associated with current methods of detecting and diagnosing VAP, vastly improving clinical outcomes and reducing treatment cost.

Accordingly, a monolithic, 3D IC can be used to diagnose ventilator-associated pneumonia (VAP) that include culturing bacteria from a patient susceptible to VAP. It can do this by detecting at least one volatile organic compound (VOC) emitted by the bacteria, and/or an exogeneous agent administered thereto, with a device. The bacteria can include, but are not limited to, *Escherichia coli, Proteus mirabilis, Moraxella catarrhalis, Serratia marcescens, Klebsiella pneumoniae, Burkholderia cepacia, Acinetobacter baumannii, Streptococcus pneumoniae, Stenotrophomonas (Xanthomonas) maltophilia, Aspergillus niger, Neisseria*

*lactamica, Streptococcus pyogenes, Pseudomonas aeruginosa, Staphylococcus aureus, Haemophilus influenzae,* and/or the like. A clinician can use this VOC detection to diagnose the patient as having VAP, e.g., by comparing the measurements of the patient's exhalations with the VOC(s) to a baseline exhalation measurement of the same patient (e.g., when the patient is healthy). Further, a clinician can also use the VOC detection and/or any suitable data from the device to make patient care decisions such as, for example, which anti-microbial treatment to employ, changing ventilator settings, endotracheal tube cuff inflation, epiglottal suctioning, and/or any aspect of a mechanical ventilation care routine that can reduce the likelihood of a patient contracting VAP, or contacting a more severe case of VAP.

If desired, the electronic nose can be combined with or inserted into a mechanical ventilator used by the patient for continuous monitoring of the patient's exhalations. The monolithic, 3D IC can be placed in the ventilator tubing that receives air exhaled by the patient. In this manner, in-situ evaluation of patient breath is made possible. Accordingly, such a system can include a ventilator to circulate air to a user (i.e., to and from the user's lungs), and a device that is coupled to the ventilator to receive gas exhaled by the user. FIG. 16 illustrates an example ventilator 1610 that includes a monolithic, 3D IC 1620 as described herein in an expiratory line 1630 of the ventilator. In some scenarios (not shown), the IC 1620 can be integrated into a preexisting sensor compartment or housing 1640 of the ventilator 1620.

The monolithic, 3D IC, which can be structurally and/or functionally similar to the device 100, can sense and identify the components of the gas as described above. This can include, but is not limited to, sensing VOCs with the monolithic, 3D IC when places in an expiratory circuit on the ventilator, sensing VOCs with a monolithic, 3D IC from exhalate taken from an endotracheal tube attached to the patient, sensing VOCs with a monolithic, 3D IC that is inserted into the endotracheal tube to sample VOCs from the inside of the endotracheal tube that is often colonized by bacteria, and from a monolithic, 3D IC coupled to any device that can be inserted into the lungs to sample VOCs directly from the lungs (e.g., on a bronchoscope) on a person on mechanical ventilation.

Monolithic, 3D ICs with Multiple Processing and Memory Layers

FIG. 10 illustrates another example device 1000 that can be functionally similar to the device 100. The device 1000 includes a sensing layer 1010 that can be similar to the sensing layer 110, and include over a million CNFETs. The device 1000 also includes multiple memory/data storage layers of RRAM 1020 that are interweaved with multiple processing layers 1030. Millions of nanoscale wires can establish connectivity between individual CNFETs and RRAMs, and between RRAMs and corresponding processing units. Such extensive connectivity can enable capture and processing of terabytes of information/second, including on-device storage and real-time computation/identification of gaseous components.

FIG. 11 illustrates a portion of another example device 1100 that can be structurally and/or functionally similar to the device 100. The device 1100 includes a sensing layer 1110 having a million CNFETs, where 1000 CNFETs are functionalized with the same functional material, resulting in 1000 blocks of CNFETs (FIG. 11 shows 16 such blocks) with 1000 different functionalizations $1115_1$, $1115_2$, $1115_3$, $1115_4$, ..., $1115_{1000}$.

The following example protocol is employed to capture the data shown in FIGS. 12-14.

Data Capture—Arrays of CNFET VOC sensors (256 CNFET VOC sensors per chiplet) were fabricated, and each chiplet is diced and packaged. These packages are inserted into a custom "electronic petri dish" lid, which contains the interface circuitry required to bias and record the current-voltage characteristics of all CNFET VOC sensors on each chiplet. To characterize a particular type of CNFET VOC sensor, all 256 CNFET VOC sensors on a chiplet are coated with the same functionalization, and the packaged chiplet is inserted into the electronic petri dish lid. The electronic petri dish lid is then placed over one of 15 different cultured bacteria. Each cultured bacteria is plated at clinically-relevant concentrations of $10^5$ colony forming units and cultured for 12 hours prior to measuring. To sample the bacteria VOC byproducts, the culture plates are removed from incubation and allowed to cool for 10 minutes, then the lids are removed and the plates are allowed to vent for another 5 minutes. The electronic petri dish lid is then placed over the bacteria culture for 30 seconds for the headspace to accumulate VOCs, followed by measuring the CNFET VOC sensors. This protocol is repeated to test each of the 100 functionalizations with each of the 15 bacteria.

Full-data Visualization—To visualize the information in the entire library captured from each bacteria, "pictures" of the response of the sensors to the VOCs generated from each bacteria are formed. Examples are shown in FIGS. 13D-F. Each picture is comprised of 100 sub-arrays (one per functionalization), with each sub-array containing 256 horizontal lines (each horizontal line is the response from a single CNFET VOC sensor, as the example shown in FIG. 12A). Every horizontal line contains 3746 measurements, corresponding to the measured drain current at 3746 different biasing conditions ($V_D$ varies from 0 to 1V and $V_G$ varies from −2 to 2V).

Classification—To classify the fingerprints associated with different bacteria VOC byproducts, image classification machine learning is employed. Here, images are classified using a bag of visual words approach, though alternative approaches can be easily adapted. To perform this training and classification, the Speeded-up Robust Features (SURF) descriptor is used to extract descriptors from the images, follows by k-means clustering to determine the top 500 features for classifying 21 different classes (blank *Brucella* horse blood media+blank MacConkey media+15 different bacteria on *Brucella* horse blood media+3 bacteria on MacConkey media+blank measurement in air). Each cluster center represents a feature, or visual word. The multiclass classifier is formed using binary support vector machine (SVM) classifiers in an error-correcting output codes (ECOC) framework). To test the classifier, 600 test fingerprints are classified (30 test fingerprints from each class).

Image generation for classification—To avoid overfitting, the 256 copies of each type of CNFET VOC sensor is a plot into two sets of CNFET VOC sensors (128 copies for a training set, and 128 copies for a validation set). This ensures there is no overlap in the sensors used for training and validation. To form multiple pictures, 64 sensors from the set of 128 sensors are randomly drawn, for each type of CNFET VOC sensor (the full picture is still formed by combining all 100 sub-arrays comprising now of 64 CNFET VOC sensors each into a single larger picture). The image classification machine learning described above is used to train on 30 pictures of each bacteria, and then attempt to classify 600 pictures of the bacteria. FIG. 14 shows the results of the classification. The ability to distinguish between samples that have bacteria or do not have any bacteria is 100% accurate (600/600 pictures accurately assigned as either having bacteria versus blank controls). The ability to determine the exact strain of the causative organism across all 18 organisms is 99.5% (597/600 perfectly identified organisms).

Turning to FIGS. 12-14 now, FIG. 12A illustrates example output of an individual CNFET gas sensor as a portion of the output from a sensing layer as disclosed herein. Specifically, FIG. 12A is a plot of current through through a single CNFET (with current value specified by the color) at different values of gate voltage $V_G$ and/or drain voltage $V_D$, which vary over time (X-axis). The plot is a result of exposure of the CNFET sensor to a gas containing VOCs produced by the bacteria *Klebsiella pneumoniae*. The functionalization material of the CNFET sensor is copper(II) 2,9,16,23-tetra-tert-butyl-29H,31H-phthalocyanine.

FIG. 12B illustrates example output of a subarray of CNFETs that includes 1000 individual CNFET gas sensors, each functionalized as described for FIG. 12A, and each having an output as generally illustrated in FIG. 12A. Such redundancy of the same type of CNFET gas sensor (i.e., having the same functionalization) can reduce variability across sensors and provide a more accurate understanding of the general response of such a sensor.

FIG. 12C illustrates example output of an array of CNFETs that includes multiple subarrays as illustrated in FIG. 12B, and having an output as generally illustrated in FIG. 12B. Each CNFET subarray can be functionalized differently—for example, there may be 1000 subarrays of 1000 CNFETs each. Alternatively, the CNFET subarrays may be functionalized to provide redundancy or greater sensitivity—for example, there may be 1000 CNFET subarrays that are similarly functionalized. Other arrangements are also possible. For instance, there may be many CNFET subarrays functionalized to detect harder-to-detect compounds and fewer CNFET subarrays functionalized to detect easier-to-detect compounds.

FIG. 13A is an example output of a subarray (i.e., having multiple CNFETs with the same functionalization material, copper(II) 2,9,16,23-tetra-tert-butyl-29H,31H-phthalocyanine) when exposed to air, providing a 'baseline' or 'control' against with other test samples can be evaluated. FIG. 13B is an example output of the same subarray with the same functionalization material when exposed to a gas containing components released by a first bacterial species, *P. Aeruginosa*. Both computationally and visually, the output of FIG. 13B is readily distinguishable from that of the baseline in FIG. 13A. FIG. 13C is another example output of the same subarray as FIG. 13A when exposed to a gas containing components released by a second bacterial species (*S. Aureus*) that is different than the first. Again, both computationally (e.g., using machine learning approaches as disclosed herein) and visually, the output of FIG. 13B is readily distinguishable from that of the baseline in FIG. 13A, and from that of the first bacterial species.

FIGS. 13D, 13E, and 13F are example outputs of a complete array of CNFET sensors of a sensing layer when exposed to gases containing components released by the bacterium *Pseudomonas aeruginosa, Staphylococcus aureus*, and *Haemophilus influenzae*, respectively. Again, both computationally and visually, the output of each is readily distinguishable from the others.

FIG. 14 is an evaluation/confusion matrix that illustrates accuracy of bacterial classification, such as can be performed with 256 CNFET gas sensors in each functionalization material using a support vector machine (SVM) executed in the processing layer of the device. The SVM is trained with training data (e.g., 128 response patterns) obtained from half of the CNFET gas sensors in the sensing layer, and classification is performed using test data (i.e., 128 response patterns) obtained from the other half of the CNFET gas sensors. In this example, there is no overlap between the training data and the test data. The SVM performs binary bacterial classification (i.e., bacteria vs. no bacteria) with greater than 99.5% accuracy and is able to ascertain the exact bacterial species with about 92% accuracy. In the case of *E. coli*, for example, the SVM classifies it accurately almost 100% of the time. Overall, FIG. 14 illustrates classification between 21 classes of samples—18 different strains of bacteria, air, blank *Brucella* horse blood media, and blank MacConkey media.

FIGS. 15A-15C illustrate example operation of an example device 1500 (FIG. 15A) during typical use. The device 1500, which can be similar to the device 100, includes an input/output sensing layer 1510 (green), a memory layer 1520 (blue), a computation/processing layer 1530 (red), interconnects 1540 for memory access by the layer 1530, and an interface 1550 (purple) to the processing layer 1530. FIGS. 15B and 15C are shaded color-coded for correspondence to FIG. 15A, with FIG. 15B illustrating that the inputs to the device 1500 (e.g., via the interface 1550) are memory addresses, control signals (the 'select' signal for the multiplexer in the interface subsystem 1550, the control voltages to the sensing circuits $V_{G1}$ and $V_{G2}$ of the sensing layer 1510, and the reset or read voltage applied to the RRAM $V_R$ of the memory layer 1520), and power and clock signals. Such inputs can be generated off the device 1500 and routed to the device via the interface 1550 through input/output pins. Signals with the same label ($V_R$, $V_S$, $V_{G1}$ or $V_{G2}$) are connected on the device 1550 to the same input/output pin. Wordlines (horizontal wires in the array, labelled 0 to 1,023) and bitlines (vertical wires in the array, labelled 0 to 1,023) are shown as red solid lines and purple dashed lines, respectively. The sense amplifier ('sense amp.') is the circuitry that reads the value of the RRAM memory cell, and the select signal controls the multiplexer to select which sensor amplifier is connected to the computation subsystem.

FIG. 15C illustrates operation of the device 1500 across three phases: initialization, sensing and computation. In the initialization phase, all RRAM cells in the memory layer 1520 are reset and initialized to 0; specifically, voltage is applied to reset the RRAM Vreset=−2.75 V. In the sensing phase, all CNFET gas sensors write either a 1 or a 0 (depending on how each sensor reacts with the gas) into the RRAM cell underneath directly and in parallel. In the computation phase, the CNFET row decoders and silicon interface logic in the processing layer 1530 select individual RRAM cells sequentially (by the memory addresses and control signals generated off-chip), enabling the CNFET-based classification accelerator to perform classification; voltage applied to read the RRAM Vread=1.25 V. GND is ground (0 V).

Some aspects disclosed herein are directed to a monolithic 3D IC that contains (in a sensing layer) 1000 different sensors or more, that are evenly or unevenly split between 500 functionalization materials or more. A second layer underlying the sensing layer includes a layer of transistors. The transistors can have varied functionality, including (but not limited to): (1) measuring the response of the sensors in the sensing layer (e.g., include biasing circuitry to bias the sensors, and further include analog-to-digital converters (ADCs) to measure the response of the sensors); (2) access circuitry to select (the response of) which sensor and/or combination of sensors is measured at any given point in time; and/or (3) computation to analyze the measurements of the sensors, such as using any suitable machine learning approach as described herein. The IC may also include more layers of computing and/or memory (for instance, RRAM) for further computing and data storage capabilities embedded on-chip.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of diagnosing ventilator-associated pneumonia (VAP) with a device comprising carbon nanotube field-effect transistors (CNFETs) arranged in a sensing layer, a memory layer operably coupled to the sensing layer, and a processing layer operably coupled to the memory layer, the method comprising:
culturing bacteria from a patient susceptible to VAP;
detecting at least one volatile organic compound (VOC) in emissions of the bacteria with the CNFETs in the sensing layer;
writing data generated by the CNFETs in parallel to memory elements in the memory layer;

transferring the data generated by the CNFETs in parallel from the memory elements to processing elements in the processing layer;

identifying, with the processing elements, the at least one VOC in the emissions of the bacteria based on the data generated by the CNFETs; and diagnosing the patient as having VAP based on the at least one VOC in the emissions of the bacteria.

2. The method of claim 1, wherein the device is embedded in or coupled to a culture dish used for culturing the bacteria.

3. The method of claim 1, wherein the detecting the at least one VOC further comprises:

detecting, by the processing layer, a change in a response pattern of the CNFETs.

4. The method of claim 1, further comprising identifying at least a first bacterial type in the bacteria from the patient by:

generating, by the processing layer, a set of images, each image of the set of images corresponding to a response pattern of a subset of the CNFETs to the emissions of the bacteria; and classifying, using supervised learning, the set of images as the first bacterial type of a predetermined set of bacterial types.

5. The method of claim 4, where the predetermined set of bacterial types includes one or more of: *Escherichia coli, Proteus mirabilis, Moraxella catarrhalis, Serratia marcescens, Klebsiella pneumoniae, Burkholderia cepacia, Acinetobacter baumannii, Streptococcus pneumoniae, Stenotrophomonas* (*Xanthomonas*) *maltophilia, Aspergillus niger, Neisseria lactamica, Streptococcus pyogenes, Pseudomonas aeruginosa, Staphylococcus aureus*, or *Haemophilus influenzae*.

6. The method of claim 4, wherein the supervised learning includes using one or more of: a support vector machine (SVM), artificial neural network, decision tree, or random forest.

7. The method of claim 6, wherein the supervised learning includes a SVM that has been previously trained on training response patterns associated with the CNFETs of the device.

8. The method of claim 4, wherein the CNFETs are disposed as an array of CNFETs on the sensing layer, and wherein each image of the set of images corresponds to a different subarray of the array of CNFETs, and wherein each subarray of the array of CNFETs has a different functionalization from each other subarray of the array of CNFETs.

9. The method of claim 8, wherein the functionalization of each CN FET of the array of CNFETs is non-specific to the at least one VOC to be detected.

10. The method of claim 4, further comprising:

training a machine learning model to identify the at least one VOC based on the set of images.

11. The method of claim 1, wherein the detecting the at least one VOC in the emissions of the bacteria with the CNFETs in the sensing layer comprises adjusting a bias voltage applied to at least one of the CNFETs.

12. The method of claim 1, wherein the detecting the at least one VOC in the emissions of the bacteria with the CNFETs in the sensing layer comprises recording current-voltage characteristics of the CNFETs.

13. The method of claim 1, wherein the writing the data in parallel from the CNFETs to the memory elements in the memory layer comprises transmitting the data via interlayer vias connecting the sensing layer to the memory layer.

14. The method of claim 1, wherein the transferring the data in parallel from the memory elements to the processing elements comprises transmitting the data via interlayer vias connecting the memory layer to the processing layer.

15. The method of claim 1, wherein at least one of the CNFETs is functionalized with multiple functional materials.

16. The method of claim 1, wherein the CNFETs are arranged in blocks and each of the blocks is functionalized with a different functional material.

17. The method of claim 16, wherein the different functional materials include at least 50 different functional materials.

18. The method of claim 1, wherein the device includes at least 1,000,000 CNFETs.

19. The method of claim 1, wherein the memory elements comprise resistive random access memory (RRAM) cells.

20. The method of claim 1, wherein the sensing layer, memory layer, and processing layer form a monolithic, three-dimensional integrated circuit.

* * * * *